United States Patent
Galimberti et al.

(10) Patent No.: US 11,414,383 B2
(45) Date of Patent: Aug. 16, 2022

(54) ADDUCTS FORMED FROM PRIMARY AMINES, DICARBONYL DERIVATIVES, INORGANIC OXIDE HYDROXYDES AND SP²-HYBRIDIZED CARBON ALLOTROPES

(71) Applicants: PIRELLI TYRE S.p.A, Milan (IT); POLITECNICO DI MILANO, Milan (IT)

(72) Inventors: Maurizio Stefano Galimberti, Milan (IT); Vincenzina Barbera, Milan (IT)

(73) Assignees: PIRELLI TYRE S.p.A., Milan (IT); POLITECNICO DI MILANO, Milan (IT)

( * ) Notice: Subject to any disclaimer, the term of this patent is extended or adjusted under 35 U.S.C. 154(b) by 0 days.

(21) Appl. No.: 16/347,117

(22) PCT Filed: Nov. 9, 2017

(86) PCT No.: PCT/IB2017/057004
§ 371 (c)(1),
(2) Date: May 2, 2019

(87) PCT Pub. No.: WO2018/087688
PCT Pub. Date: May 17, 2018

(65) Prior Publication Data
US 2020/0223797 A1 Jul. 16, 2020

(30) Foreign Application Priority Data
Nov. 9, 2016 (IT) .......................... 102016000013070

(51) Int. Cl.
*C07D 207/323* (2006.01)
*C07D 207/333* (2006.01)
*B82Y 30/00* (2011.01)
*B82Y 40/00* (2011.01)
*C09C 1/56* (2006.01)

(52) U.S. Cl.
CPC ..... *C07D 207/323* (2013.01); *C07D 207/333* (2013.01); *B82Y 30/00* (2013.01); *B82Y 40/00* (2013.01); *C09C 1/56* (2013.01)

(58) Field of Classification Search
CPC ........................ C07D 207/323; C07D 207/333
See application file for complete search history.

(56) References Cited

U.S. PATENT DOCUMENTS

| 2006/0045838 A1 | 3/2006 | Malenfant et al. |
| 2017/0275169 A1 | 9/2017 | Galimberti et al. |
| 2017/0226269 A1 | 10/2017 | Galimberti et al. |

FOREIGN PATENT DOCUMENTS

| CN | 104045810 A | 9/2014 |
| WO | WO 2010/102763 | 9/2010 |
| WO | WO 2015/189411 | 12/2015 |
| WO | WO 2016/023915 A1 | 2/2016 |
| WO | WO 2016/050887 A1 | 4/2016 |

OTHER PUBLICATIONS

Galimberti et al., Rubber Chemistry and Technology, vol. 90, No. 2, pp. 285-307 (Jun. 1, 2017).*
Galimberti et al., Innovative biosourced compatibilizers for carbon and whtie fillers in rubber compounds, Fall Technical Meeting of the Rubber Division, American Chemical Society, 186th, Nashville, TN, United States, Oct. 14-16, 2014 (2015), Meeting Date 2014, vol. 1, 368-409. (abstract only).*
Galimberti et al., Innovative biosourced compatibilizers for carbon and white fillers in rubber compounds, Fall Technical Meeting of the Rubber divisiona, American Chemical society, 186th, Nashville, TN, United States, Oct. 14-16, 2014, pp. 1-42.*
Galimberti et al, Universal couping agent for carbon black and silica, 196th technical meeting—Fall 2019, Date Oct. 8, 2019, Cleveland, OH, abstract only.*
International Search Report form the European Patent Office in corresponding International Application No. PCT/IB2017/057004 dated Feb. 13, 2018.
Written Opinion of the International Searching Authority from the European Patent Office in corresponding International Application No. PCT/IB2017/057004 dated Feb. 13, 2018.

* cited by examiner

*Primary Examiner* — Rebecca L Anderson
(74) *Attorney, Agent, or Firm* — Finnegan, Henderson, Farabow, Garrett & Dunner, L.L.P.

(57) ABSTRACT

Adducts are described, obtainable from the reaction product of a secondary amine and a diketone, with carbon allotropes in which the carbon is $sp^2$ hybridized, such as graphene, graphite, fullerene, carbon nanotubes and the like, and an inorganic oxide-hy-droxide. A process for preparing said adducts is also described.

17 Claims, No Drawings

ADDUCTS FORMED FROM PRIMARY AMINES, DICARBONYL DERIVATIVES, INORGANIC OXIDE HYDROXYDES AND SP²-HYBRIDIZED CARBON ALLOTROPES

This application is a national stage application under 35 U.S.C. § 371 based on International Application No. PCT/162017/057004, filed Nov. 9, 2017, and claims priority of Italian Patent Application No. 102016000113070, filed Nov. 9, 2016.

DESCRIPTION

The present invention relates to adducts obtainable from: the reaction product of a secondary amine and a diketone, with carbon allotropes, in which the carbon is $sp^2$ hybridized, and an inorganic oxide-hydroxide.

More generally the present invention relates to adducts comprising molecules with a pyrrole ring in which the nitrogen atom bears lipophilic or hydrophilic substituents, carbon allotropes in which the carbon is $sp^2$ hybridized and an inorganic oxide-hydroxide.

In a more general sense the present invention relates to adducts capable of forming dispersions of at least one carbon allotrope that contains $sp^2$ hybridized carbon atoms, in media that have different, or even very different, values of the solubility parameter, or that are hydrophilic or lipophilic. These media may be liquids of low or high viscosity or may be solids, preferably of a polymeric nature. The aim of the present invention is therefore to prepare an adduct that is a universal dispersant for a carbon allotrope that contains $sp^2$ hybridized carbon atoms, i.e. that promotes the dispersion of this carbon allotrope in media that have different, or even very different, values of the solubility parameter, or that are hydrophilic or lipophilic. A further basic aim of the present invention is as follows: the adduct that effects the dispersion of the carbon allotrope containing $sp^2$ hybridized carbon atoms must not release any chemical compound in the liquid media and in the polymer matrices with which it is mixed.

The present invention thus relates to adducts comprising compounds containing a primary amine, 1,4-diketones, at least one carbon allotrope containing $sp^2$ hybridized carbon atoms and an inorganic oxide-hydroxide.

The present invention further relates to a process for preparing the aforementioned adducts.

It is known that carbon exists in various allotropic forms, which are classified on the basis of the hybridization of the carbon atoms that make up said allotrope. In diamond, the carbon atoms are $sp^3$ hybridized. In other allotropes, the carbon atoms are $sp^2$ hybridized. Among these other allotropes, we may mention: graphene, nanographites consisting of few graphene layers (from a few units to several tens), graphite, fullerene, nanotoroids, nanocones, graphene nanoribbons, single-wall or multiwall carbon nanotubes, and carbon black, also called lampblack. Graphene is a layer of carbon atoms and thus has the thickness of a carbon atom. Graphite, carbon nanotubes and carbon black consist of graphene layers. Graphite consists of a variable number of graphene layers stacked in crystalline aggregates, with a typical spacing of about 0.34 nm. The number of stacked layers may be less than ten and may reach several thousand. Carbon nanotubes may be regarded as being formed from rolled-up graphene layers. One layer forms a single-wall nanotube, and several layers form multiwalled or multiwall nanotubes. In each of these allotropes, rings are present as the base unit. These rings may typically have 5 or 6 carbon atoms. In these rings, there are electrons in $\pi$ orbitals, delocalized on the aromatic polycyclic system. This is possible because the rings are all condensed and constitute a single system. The simplest examples of an aromatic polycondensed system are the aromatic polycycles (which include: pyrene, phenanthrene, anthracene). The carbon allotropes with $sp^2$ hybridized carbon constitute the equivalent of an aromatic polycondensed system with varying degree of planarity. For a system to be defined as aromatic, three conditions must exist: (a) the system must be cyclic, (b) the ring atoms must all have $sp^2$ hybridization and the sum of the $\pi$ electrons must satisfy Hückel's rule ($\pi=4n+2$, where n is an integer including zero), (c) the system must be planar. The requirements are all satisfied in the case of graphene. In the case of non-planar carbon allotropes, such as fullerene and carbon nanotubes, the curvature affects the condition of planarity. Such systems may, however, be defined as aromatic, and they represent an exception.

The carbon allotropes based on $sp^2$ carbon atoms of greatest interest are certainly the nanographites consisting of a few graphene layers (from a few units to several tens) and the single-wall or multiwall carbon nanotubes and carbon black. In particular, carbon black is by far the most used allotrope industrially. There is enormous interest in graphene, but its reduced availability means it is a product that is still very little used industrially.

The carbon allotropes in which the carbon is $sp^2$ hybridized, such as carbon nanotubes, graphene, graphite and carbon black, possess electrical and thermal conductivity. In particular, carbon nanotubes and graphene possess exceptional mechanical properties, and electrical and thermal conductivity. They have nanometric dimensions, i.e. of a few nanometres: one dimension, in the case of graphene, and two dimensions, in the case of nanotubes. The nanometric size and the particular geometry, lamellar in the case of graphene, tubular in the case of nanotubes, give them a large surface area and therefore the capacity to establish a large interfacial area with the matrix in which they are embedded, having a considerable effect on its properties.

The carbon allotropes can be subdivided into "nano" and "nano-structured". A chemical individual is defined as "nano" when it has at least one dimension under 100 nm. Carbon allotropes such as fullerene, carbon nanotubes, graphene and nanographites are so-called "nano" allotropes. Graphene is a layer of $sp^2$ hybridized carbon atoms, it has the thickness of a carbon atom and is thus of nanometric size. Carbon nanotubes have a diameter of a few nanometres. As stated above, graphite is formed from crystalline aggregates, formed in their turn from stacked graphene layers. When the number of stacked graphene layers is low, from less than ten to several tens, the size of the crystalline aggregate in the direction orthogonal to the layers ranges from a few nm to a few tens of nanometres. These graphites are therefore called nanographites.

On the other hand, the carbon black that has been used for more than a century for reinforcing polymer materials and for many other applications is "nano-structured". In fact it consists of fundamental particles, which have nanometric dimensions, combined to form aggregates in which these fundamental particles are held together by covalent bonds. The thermomechanical stresses typical of the action of mixing of carbon black with polymer matrices and also typical of the use of said matrices are not able to separate the aggregates into the fundamental components. Aggregation leads to the creation of voids between the fundamental particles, creating a particular structure for carbon black. The larger the quantity of voids, the larger is the structure. The definition of nano-structured filler is derived from this.

The aggregates of carbon black are larger than 100 nm. The aggregates are then joined together by van der Waals forces to create the agglomerates, which can, however, be separated into the starting aggregates by thermomechanical stresses.

Owing to their properties, carbon allotropes are used both in polymer, plastic or elastomer matrices, and in liquid media that will then form coating layers. They promote mechanical reinforcement, and thermal and electrical conductivity of the materials in which they are embedded. Improvement of the aforementioned properties is particularly good when "nano" carbon allotropes are used. Moreover, carbon allotropes in polymer matrices have a notable flame-retardant effect. In the case of polymer matrices, the carbon allotropes may be mixed directly in said matrices, forming a final product by the traditional mixing technologies, or they may form part of predispersions, typically in concentrations greater than those employed in the final product. Similarly, in the case of dispersions in liquid media, the carbon allotropes may form part of the final formulation, to be used for example for forming coating layers, or may be included in a "stock dispersion", to be used for preparing various formulations.

With all the compositions just mentioned that contain carbon allotropes, the aim is to obtain optimum distribution and dispersion of the allotropes. In the case of dispersions in liquid media, the aim is firstly to obtain stability of said dispersion, avoiding sedimentation of the allotrope. This aim is pursued both in the case of dispersions of carbon allotropes in polar media and in the case of dispersions in non-polar media. The instability of these dispersions leads to lack of development for applications on an industrial scale. These problems have been identified in particular for the "nano" carbon allotropes. In the case of polymer composites the aim is in particular to ensure optimum interaction of the allotropes with the matrix, and stable interaction in the conditions of use of the material. In fact, the greatest problem that may arise in the case of polymer composites containing carbon allotropes is insufficient interaction of said allotropes with the polymer matrix. This problem has been observed in particular for the "nano" carbon allotropes. This leads to insufficient transfer of the properties of the allotropes to the composite material and leads to instability of the dispersion of said allotropes, which tend to form aggregates, with notable impairment of the properties of the final material.

As already mentioned, the dispersions need to be stable in liquid media of low viscosity, both polar and non-polar. The polar media of low viscosity may be the solvents normally used, especially those that are environmentally friendly, such as water, alcohols, ketones, esters, and amides. Examples of alcohols are ethanol and isopropanol, examples of ketones are acetone and methyl ethyl ketone, an example of ester is ethyl acetate, and an example of amide is N-methylpyrrolidone. Obviously these solvents are characterized by different polarity. However, it may be desirable to prepare dispersions in non-polar hydrocarbon solvents, for example hexane, heptane, cyclohexane, as well as aromatic, for example toluene. Although some of these solvents might not be environmentally friendly, it may nevertheless be necessary to prepare the dispersion of the carbon allotropes in these solvents, which are capable for example of dissolving various kinds of polymer materials.

Moreover, as mentioned above, stable dispersion and stable interaction of the carbon allotropes must also be achieved in matrices of a polymeric nature. The polymers may be either amorphous or semicrystalline. In the case of polymers of a polar nature, these polymers may have a group of a polar nature in one or in all the repeating units. Examples of polymers with a polar group in every repeating unit are: polyurethanes, polyamides, polyethers, polyesters, polycarbonates, poly(vinyl esters), poly(vinyl alcohol). Examples of polymers that do not contain a polar group in every repeating unit are:

copolymers of ethylene with polar monomers such as vinyl acetate, vinyl(alcohol). Other examples of polymers that do not contain a polar group in every repeating unit are polymers in which the polar group was introduced by a grafting reaction. Examples of these polymers that can undergo a grafting reaction are polyolefins, such as poly (ethylene) and poly(propylene), ethylene-propylene copolymers, polymers derived from dienes, on which an anhydride has been grafted, such as maleic anhydride or itaconic anhydride, or on which an ester such as ethyl maleate has been grafted, or on which a mixture of an anhydride and an ester has been grafted. Then there are polymers that are of a non-polar nature but contain polar groups as chain ends, for example natural rubber, or poly(1,4-cis-isoprene), which is derived from the plant *Hevea brasiliensis*. Another example of a polymer of a non-polar nature but with a polar end group is the copolymer of styrene and butadiene, for example obtained by anionic catalysis, and having a polar end group.

Examples of polymers having a non-polar nature are well known in the field of materials, since such polymers are the most important, widely-used products. Only as examples, we may mention polyethylene, polypropylene, the copolymers of ethylene and propylene, and the homopolymers and copolymers of styrene.

There are publications and patents in the prior art that discuss the dispersion of allotropes in matrices of various kinds.

Composites based on carbon nanotubes are described in "Carbon nanotube-polymer interactions in nanocomposites: A review", Composites Science and Technology 72 (2011) 72-84. Composites based on graphene and nanographites are described in "Graphene-based polymer nanocomposites." Polymer, 52(1), 5-25 (2011). In both cases carbon allotropes are used for preparing composites both in polar polymers such as polyacrylates and epoxy resins and non-polar polymers such as poly(ethylene) and poly(styrene). Dispersions of carbon nanotubes in elastomer matrices are described in "Multiwall carbon nanotube elastomeric composites: a review" Polymer, 48(17), 4907-4920 (2007) and in "The Role of CNTs in Promoting Hybrid Filler Networking and Synergism with Carbon Black in the Mechanical Behavior of Filled Polyisoprene" Macromol. Mater. Eng., 298, 241-251 (2012). Dispersions of nanographites in elastomer matrices are also reported, for example in "Filler Networking of a Nanographite with a High Shape Anisotropy and Synergism with Carbon Black in Poly(1,4-Cis-Isoprene)—Based Nanocomposites" Rubber Chemistry and Technology, Vol. 87, No. 2, pp. 197-218 (2014). All these composites do indeed have carbon allotropes dispersed at the level of the individual constituent particles, or at the level of the individual nanotubes or of the individual lamellae of graphene or of aggregates with few graphene layers, but they also have agglomerates. In particular, in "Filler Networking of a Nanographite with a High Shape Anisotropy and Synergism with Carbon Black in Poly(1,4-Cis-Isoprene)—Based Nanocomposites" Rubber Chemistry and Technology, Vol. 87, No. 2, pp. 197-218 (2014) it is shown that the nanographite aggregates tend to aggregate further, i.e. to be made up of several graphene layers, when embedded in the crosslinked elastomer composite. Moreover, in the publication *Macromol. Mater. Eng.*, 298, 241-251 (2012) it is clearly shown that the carbon nanotubes are fragmented during the mixing operation, drastically reducing their length. In the publication A. Das, K. W. Stockelhuber, R. Jurk, M. Saphiannikova, J. Fritzsche, H. Lorenz, M. Kuppler, G. Heinrich, Polymer 2008, 49, 5276-5283, fragmentation of the nanotubes in a matrix formed from a mixture of poly(1,4-cis-butadiene) and poly(butadiene-co-styrene) is only partially avoided by predispersing the carbon nanotubes in ethanol. In the publication L. Bokobza, M. Kolodziej, Polym Int 2006, 55, 1090-1098, mixing of the carbon nanotubes in an aromatic solvent such as toluene is employed, since this solvent is able to dissolve the polymer in which the nanotubes are to be mixed. However, images obtained by scanning electron microscopy still show the presence of agglomerates in the composite prepared with a matrix of natural rubber. Dispersion of carbon black in polymer matrices, for example elastomer matrices, is achieved through the use of mechanical energy of mixing. It can be summarized as follows, as described in the literature relating to the dispersion of carbon allotropes. It is not possible to disperse carbon allotropes with the same degree of efficiency in media of different natures. There are no stable dispersions of unmodified carbon allotropes in environmentally friendly polar solvents. Dispersions in aromatic solvents, which might in principle be efficient, are only being tested at the laboratory level and are not being developed industrially, for obvious reasons connected with the use of aromatic substances. In the case of dispersions of carbon allotropes in polymer matrices, acceptable results are only obtained by using a high level of mechanical energy, but this leads for example to breakage of the carbon nanotubes and to reduction of the molecular weight of the polymers that make up the matrix in the case of composites, especially elastomer composites, based on carbon black.

Thus, it is universally accepted that, so as to be able to obtain a stable dispersion both in liquid dispersants of low to medium viscosity and in polymers, the carbon allotropes must be modified either by chemical modifications that lead to the formation of covalent bonds with functional groups, resulting in functionalization of the allotropes, or by chemical modifications of the non-covalent type, or supramolecular interactions.

WO2010/102763 describes compositions based on semicrystalline polyurethane, in which carbon nanotubes are dispersed in order to improve their characteristics. In this case the modifications take place through the use of polymer chains grafted onto the carbon allotrope, which allow dispersion in polyurethane. In this case, however, the interaction between the polyurethane and the allotrope is not stable, as it only occurs owing to the carbonyl group present in the polymer. In the absence of stable interaction, the carbon nanotubes dispersed in the polymer matrix, or in a liquid medium, tend to sediment and to separate from the medium, creating zones richer in nanotubes and zones depleted of nanotubes, therefore altering the characteristics of the product. It is obvious that this solution is not of general applicability, i.e. it can only be applied in the case of polyurethane matrices.

US2006/0045838 describes adducts between carbon nanotubes and soluble polymers selected from poly(thiophene), poly(pyrrole), poly(fluorene), poly(phenylene), poly(phenylene ethynylene), poly(phenylene vinylene), poly(alkylidene fluorene), poly(fluorene bithiophene) and combinations thereof. In this case too, the modifier is of a polymeric nature. The nature of the polymers is clearly lipophilic and this means selecting organic solvents such as chloroform for dissolving them, which are solvents that are critical from the viewpoint of impact on the environment and on health. Moreover, these adducts do not offer the possibility of stable dispersions in environmentally friendly polar solvents, for example in aqueous solvents. In this solution, it is first necessary to synthesize a polymer, and then prepare the adduct. Moreover, this solution is not of general applicability either, since it is limited to non-polar environments.

Moreover, it is known to be possible to disperse carbon allotropes in aqueous solvents. Surfactants such as sodium dodecyl sulphate are used, as reported in "SDS Surfactants on Carbon Nanotubes: Aggregate Morphology" ACS Nano, 2009, 3 (3), pp 595-602. In this case, advantage is taken of the interaction between the dodecyl substituent and the allotrope, while the salt guarantees dispersion in water. "Decoration of carbon nanotubes with chitosan" Carbon, 43(15), 3178-3180 (2005) describes the dispersion of carbon nanotubes in acid solutions (pH=5) by preparing the adduct of the carbon nanotubes with chitosan. In this case, the interaction between the ammonium cations and the $\pi$ systems of the nanotubes is utilized. It is clear that these modifiers are effective in polar environments, but not in the case of non-polar environments. Moreover, they impair the properties of the allotropes, and do not contribute in any way to the electrical and thermal conductivity of the allotropes themselves.

Moreover, the possibility of solubilizing a polymer with aromatic repeating units in an aqueous environment is known.

For example, a water-soluble polymer of a substituted pyrrole is obtained by electro-oxidative polymerization of potassium 3-(3-alkylpyrrol-1-yl)propanesulphonates, as reported in "Lamellar Conjugated Polymers by Electrochemical Polymerization of Heteroarene-Containing Surfactants: Potassium 3-(3-Alkylpyrrol-1-yl) propanesulfonates" Chem. Mater. 1994, 6, 850-851. A water-soluble polypyrrole is reported in "A Water-Soluble and Self-Doped Conducting Polypyrrole Graft Copolymer", *Macromolecules* 2005, 38, 1044-1047. A poly(sodium styrenesulphonate-co-pyrrolylmethylstyrene) copolymer is used as a precursor for polymerization of the pyrrole contained as a side group in the polymer with other units of unsubstituted pyrrole.

In these two examples it is necessary to synthesize a substituted pyrrole or a polymer containing a pyrrole ring. The yields of these reactions are not high and they are not carried out starting from ingredients from renewable sources. Moreover, a reaction of post-treatment is required. Finally, this synthesis scheme leads to the production of molecules that are then stable in hydrophilic environments.

The post-treatment of polypyrroles is also reported in *"Synthesis and characterization of water soluble polypyrrole doped with functional dopants"* Synthetic Metals 143 289-294 (2004). Sulphonation of a polypyrrole is carried out. In this case, it is not possible to obtain a polymer containing aromatic rings like that of the pyrrole and polar groups directly by polymerization. The polymerization to polypyrrole must be carried out first, and then the post-treatment. In this case too, hydrophilic polypyrroles are obtained by a sulphonation reaction.

The publication RSC Adv., 2015, 5, 81142-81152 describes a molecule containing a pyrrole ring, and it is reported that this molecule forms stable aqueous solutions of nanographites containing various numbers of graphene layers stacked to form a crystalline network. This molecule is 2-(2,5-dimethyl-1-H-pyrrol-1-yl)-1,3-propanediol and it is also called serinol pyrrole. The molecule is obtained by the synthesis of 2-amino-1,3-propanediol (also called serinol) with 2,5-hexanedione. It is reported that the synthesis between serinol and hexanedione takes place in 3 steps. First at room temperature for 6 hours, obtaining a tricyclic compound as intermediate, 4a,6a-dimethyl-hexahydro-1,4-dioxa-6b-azacyclopenta[cd]pentalene. Then the tricyclic intermediate is kept under vacuum for 2 hours and finally is heated at 180° C. for 50 minutes, obtaining serinol pyrrole.

The synthesis of serinol pyrrole is also described in the publication Polymer, Volume 63, 20 Apr. 2015, Pages 62-70. The same procedure and the same conditions are reported.

The synthesis of serinol pyrrole is also described in the Conference Proceedings Fall 186$^{th}$ Technical Meeting of the Rubber Division of the American Chemical Society, Inc. Nashville (TN) Oct. 14-16, 2014. In this publication, the tricyclic compound is held at 180° C. for 8 hours.

The synthesis of serinol pyrrole is also described in patent application WO 2015/189411A1, in which, in example 1, it is stated that a mixture of serinol and of the diketone was stirred for 6 hours at 25° C. and was then heated at 130° C. for 7 hours. Still in WO 2015/189411A1, other reaction conditions are also reported: a mixture of serinol and hexanedione is heated directly for 8 hours at 130° C. or for 30 minutes at 150° C., in Examples 2 and 3 respectively.

Both in the publication and in patent application WO 2015/189411A1 it is described that, at the end of the reaction, serinol pyrrole is obtained with high chemical purity by distillation at reduced pressure. In the publication, it is reported that the total yield of the reaction is equal to about 95%.

The examples of synthesis of serinol pyrrole reported in the publications Polymer, Volume 63, 20 Apr. 2015, Pages 62-70, RSC Adv., 2015, 5, 81142-81152, Conference Proceedings Fall 186$^{th}$ Technical Meeting of the Rubber Division of the American Chemical Society, Inc. Nashville (TN) Oct. 14-16, 2014 and in patent application WO 2015/189411A1 thus seem to show that it is possible to obtain this molecule with high yield, by a reaction carried out in a simple manner without adding solvents or catalysts. However, the reaction takes place at high temperature and it is necessary to maintain the high temperature for times of at least tens of minutes. Moreover, distillation is required to obtain the desired compound in a chemically pure state. It is known in chemistry that a catalyst can be used in order to make a reaction take place at a lower temperature. The reaction for the synthesis of serinol pyrrole starting from serinol and hexanedione is a so-called Paal-Knorr reaction. This reaction uses acid catalysis. In fact, in patent application WO 2015/189411A1 it is stated "For example the article with the title "*Paal-Knorr pyrrole synthesis using recyclable amberlite ir 120 acid resin*" by Aarti Devi et al. (Synthetic Communication, 42: 1480-1488, 2012) describes a process for the synthesis of pyrroles in which an acid resin of amberlite ir 120 is used as catalyst". Moreover, still in patent application WO 2015/189411A1 it is stated: "The article with the title "*novel heterotricyclic system: 2,6-dioxa-* and *2-oxa-6-thia-10-azatricylo*[5.2.1.04,10] *decane . . .* " by H. Smith Broadbent et al. (Journal of Heterocyclic Chemistry, 1976, volume 13, No. 2, pages 337-348), describes a process for the synthesis of serinol pyrrole or derivatives thereof substituted in the alpha position, in which a diketone is reacted with serinol in the presence of solvents such as toluene or heptane, in the presence of acid catalysts that promote their reaction."

However, patent application WO 2015/189411A1 actually aims to avoid the use of acid catalysts. In fact, regarding the use of an acid resin of amberlite ir 120, in the article Synthetic Communication, 42: 1480-1488, 2012 it is written: "This process, despite the high yields of pyrroles that form, has an important drawback connected with the presence of the catalyst, which must be removed from the compound by means of subsequent purifications and distillations, to avoid the compound being impure and thus unusable, especially in the pharmaceutical field, which is the actual aim". Moreover, regarding the use of acid catalysis, in the article Journal of Heterocyclic Chemistry, 1976, volume 13, No. 2, pages 337-348 it is written: "However, this process has the drawback of supplying a mixture of products, in which there is a small amount of serinol pyrrole. It is a process characterized by low selectivity. Moreover, the serinol pyrrole is diluted in organic solvents, which have to be removed, and which are pollutants for the environment and for humans." In conclusion, acid catalysts may promote conversion of the reagents but adversely affect the yield of the reaction to a compound with a pyrrole ring, lowering the selectivity. Moreover, they have to be removed from the mixture of products.

What is stated in the prior art regarding the synthesis of compounds that contain a pyrrole ring, starting from a compound that contains an amine and from a diketone, thus teaches that the reaction takes place with high yields only at high temperatures and that the use of a catalyst promotes conversion of the reactants but may also promote the formation of by-products, reducing the selectivity. Moreover, the catalyst must be removed from the mixture of products.

Patent application WO 2015/189411A1 also describes the synthesis of serinol pyrrole on carbon allotropes, such as multiwall carbon nanotubes (example 7), and graphite (example 8). In these examples 7 and 8, the reaction is carried out at 120° C. for 50 minutes, supplying serinol and hexanedione on the allotrope in the absence of solvents. At the end of the reaction, deuterated water is added, stirring manually for 2 minutes, at room temperature. After filtration of the suspension, analysis by nuclear magnetic resonance shows that the liquid consists of serinol pyrrole. It is therefore clear that the reaction carried out in situ at high temperature does not give an adduct between carbon allotrope and serinol pyrrole that is sufficiently stable so that the serinol pyrrole cannot be extracted, since it is extracted by simple immersion of the adduct in water at room temperature.

Patent application WO 2015/189411A1 also describes the synthesis of serinol pyrrole on graphite oxide. The graphite oxide was prepared as described in Macromol. Chem. Phys. 214 (17) (2013) 1931-1939. In this case, the graphite oxide is clearly a modified carbon allotrope and also performs the function of an acid catalyst. The reaction is carried out by supplying serinol and hexanedione in the absence of solvents, and the reaction takes place at room temperature for 60 minutes. After this time, water is added (5 ml) and it is stirred for 3 hours at room temperature. The resultant mixture is collected, and filtered on silica, using ethyl acetate as eluent. Analysis of the extract by nuclear magnetic resonance shows that the liquid extracted consists of serinol pyrrole. There is no information on the yield of the reaction. Thus, graphite oxide is used for performing the reaction at a lower temperature. However, it is well known that the reaction for obtaining graphite oxide from graphite is complex, as is well illustrated in the literature with examples in *Macromol. Chem. Phys.* 214 (17) (2013) 1931-1939. Moreover, the graphite oxide must be separated from the product.

It is clear from the literature cited that so-called serinol pyrrole is a hydrophilic substance, and is water-soluble. Therefore it does not appear to be a substance capable of dispersing a carbon allotrope in a lipophilic medium. Therefore this substance is not effective for dispersing a carbon allotrope in media having a different solubility parameter.

Moreover, a molecule such as serinol pyrrole is not commercially available. This poses obvious problems from the standpoint of industrial development, which may be summarized as follows. Firstly, large-scale synthesis of this molecule requires appropriate research. In fact, patent application WO 2015/189411A1 describes the synthesis in the absence of solvents. In the case when this synthesis reaction has a large enthalpy contribution, it would be necessary to take this accurately into account when increasing the scale of synthesis. For example, if the reaction were exothermic, in the absence of solvent there could be a so-called "runaway reaction". Moreover, a safety data sheet is not available for this molecule. This prevents its use on an industrial scale. It is known that in Europe, (CE) Regulation No. 1907/2006 of the European Parliament and of the Council dated 18 Dec. 2006 is in effect concerning the registration, evaluation, authorization and restriction of chemicals, known as the REACH regulation (Registration, Evaluation, Authorization and Restriction of Chemicals). A substance such as serinol pyrrole would have to undergo a long series of analyses and checks before being used in accordance with this regulation.

The adduct between serinol pyrrole and a carbon allotrope is produced in the publication RSC Adv., 2015, 5, 81142-81152 by various methods. In a first method, graphite is put in acetone at room temperature, the suspension is sonicated for 15 minutes and a solution of serinol pyrrole in acetone is then added. The resultant suspension is then sonicated for a further 15 minutes. The solvent is removed at reduced pressure and the mixture of graphite and serinol pyrrole is treated in a planetary ball mill with the jar rotating in a horizontal plane, at 300 rpm for 6 hours. The mixture is then put on a filter and washed with distilled water 6 times. After washing, 9.8 grams is obtained from 10.87 grams of mixture. In a second method, a mixture of the carbon allotrope and serinol pyrrole is prepared by the same procedure. Then the mixture is heated at 130° C. for 6 hours. Three washings with distilled water are carried out on a filter and, after washing, 5.86 grams is obtained from 6.116 grams of mixture. The method that uses a ball mill is also reported in the Conference Proceedings Fall 186$^{th}$ Technical Meeting of the Rubber Division of the American Chemical Society, Inc. Nashville (TN) Oct. 14-16, 2014.

These examples relating to the formation of the adduct between graphite and serinol pyrrole demonstrate that serinol pyrrole does not remain completely bound to the allotrope, as it can be extracted by simple washing with water at room temperature.

From what is reported in the literature, it is clear that the interaction between serinol pyrrole and a carbon allotrope, even in the adduct produced starting from serinol pyrrole that has already been synthesized, is not sufficiently stable to prevent extraction of the serinol pyrrole from said adduct.

Moreover, only serinol is presented in the literature as a molecule for forming the compound with the pyrrole ring by the Paal-Knorr reaction with diketone compounds. This is not to say that there is no teaching in the literature for forming pyrrole rings by the Paal-Knorr reaction with other amino compounds as well: the Paal-Knorr reaction is well described. However, it may be said that the teaching of the prior art is as follows: a molecule that contains a pyrrole ring and hydrophilic groups is useful for an adduct with a carbon allotrope. In this respect, serinol is a molecule which, although not unique, is certainly to be selected preferentially.

It would therefore be desirable to be able to prepare stable dispersions of carbon allotropes both in liquid media and in polymer matrices, the liquid media and the polymer matrices having a hydrophilic or lipophilic nature.

It would also be desirable to prepare said stable dispersions by supplying, in the liquid media or in the polymer matrices, adducts of the carbon allotropes with compounds that contain functional groups capable of interacting with the aromatic rings of the carbon allotropes—functional groups such as, for example, groups containing 7 electrons such as aromatic rings or carbonyls, or ammonium groups, or even only lipophilic groups.

It would also be desirable for the compounds that form the adducts with the carbon allotropes to comprise both the functional group that promotes interaction with the carbon allotrope, and other functional groups that promote interaction with the liquid media or the polymer matrices, whether they are hydrophilic or lipophilic.

It would also be desirable for the family of compounds that form the adducts with the carbon allotropes to be characterized by just one type of functional group that promotes interaction with the carbon allotrope, thus able to provide reproducible interaction between the compound and the allotrope, and by various types of functional groups that promote interaction with the liquid media or the polymer matrices, also allowing preparation of stable dispersions in liquids and matrices of a hydrophilic or lipophilic nature.

It would also be desirable for the functional groups contained in the compound that forms the adduct with the carbon allotrope, which are functional groups capable of promoting interaction with the liquid media or the polymer matrices, also to be capable of giving rise to chemical reactions, for example polymerization reactions or reaction with other chemical compounds that would lead to various types of functional groups.

It would also be desirable if the compounds used for preparing the adducts with the carbon allotropes do not reduce the properties of the carbon allotropes, for example the electrical conductivity. It would thus be desirable that the compounds used for preparing the adducts with the carbon allotropes do not substantially alter the hybridization of the carbon atoms of the allotropes.

It would also be desirable for the reaction between the compound and the carbon allotrope to be simple and reproducible, to be carried out in the context of easy experimental conditions, to be carried out in accordance with the principles of green chemistry, to be characterized by a high yield, and not to give rise to by-products. It would thus be desirable to be able to use simple, environmentally friendly techniques for synthesis and preparation.

It would also be desirable to be able to use a variety of preparation techniques.

It would in particular be desirable to be able to carry out the reaction between the allotrope and the compound, for forming the adduct, at low temperature. In that case, it would be desirable for this reaction to take place without having to add further chemicals, which might remain in the adduct and then migrate into the final compound or act as an unwanted catalyst, giving rise to further chemical reactions.

If it should be necessary to add a substance to promote formation of the adduct at low temperature, it would be desirable for this substance to be readily tolerated by the final compound or even to be a substance that is provided in many composites in which a carbon allotrope is incorporated.

It would be desirable for the reaction for forming the adduct to be carried out on the allotrope itself, thus removing a basic step of the process, such as that of synthesis and isolation of the compound.

It would be desirable that the compounds that form the adducts with the carbon allotropes are not released and cannot be extracted from said adducts, a possibility that might arise when there is weak interaction between the compound and the adduct, and when this interaction has not been established and the compound is simply adsorbed on the surface of the allotrope. When the reaction of formation of the compound that forms the adduct with the allotrope is carried out on the allotrope itself, it would be desirable that the reagents that will form the compound that forms the adduct are not released from the adduct. In fact, as already stated for the compound that forms the adduct, even these reagents might for example be undesirable in the composites in which the adduct will be incorporated, if they are reactive with other ingredients or if they might impair their properties.

It would be desirable that the compounds capable of stably interacting with carbon allotropes were products obtained from renewable sources, preferably of second generation, or that do not have an effect on the food cycle.

For preparing dispersions that are stable both in liquid media and in polymer matrices, it would be desirable to be able to use environmentally friendly solvents such as alcohols, ethers, esters and, ideally, water, and it would be even more desirable, for preparing dispersions that are stable in polymer matrices, to avoid the use of any type of solvent.

It would finally be desirable that the structures used should make it possible to obtain stable dispersions of carbon allotropes that maintain their characteristics over time.

One aim of the present invention is therefore to provide stable dispersions of carbon allotropes both in liquid media and in polymer matrices, the liquid media and the polymer matrices having a hydrophilic or lipophilic nature.

Another aim of the present invention is to provide stable adducts between a carbon allotrope in which the carbon is $sp^2$ hybridized and a compound containing functional groups capable of interacting with the aromatic rings of the carbon allotropes.

A further aim of the present invention is to identify compounds capable of forming adducts with the carbon allotropes, that comprise both the functional group that promotes interaction with the carbon allotrope and other functional groups that promote interaction with the liquid media or the polymer matrices and that are capable of promoting further chemical reactions, giving rise to new functional groups and/or to polymers.

A further aim of the present invention is to identify a family of compounds characterized by a functional group capable of establishing interaction with the carbon allotrope and thus able to generate the adduct, and by a variety of functional groups, capable of promoting interaction with the liquid media or the polymer matrices and also able to promote further chemical reactions, giving rise to new functional groups and/or to polymers.

Another aim of the present invention is to form a stable adduct between a carbon allotrope and a compound as described above without substantially altering the hybridization of the carbon atoms of the allotropes and thus without substantially altering their properties.

Yet another aim of the present invention is to carry out the reaction between the compound and the carbon allotrope simply and reproducibly, with simple experimental conditions, in accordance with the principles of green chemistry, and thus using simple, environmentally friendly techniques. A further aim of the present invention is to carry out the reaction of formation of the allotrope with high yield, without formation of by-products.

A further aim of the present invention is to carry out the reaction for forming the compound that will form the adduct with the carbon allotrope on the allotrope itself, thus removing a basic step of the process, such as that of synthesis and isolation of the compound.

Another aim of the present invention is to prepare an adduct between a compound and a carbon allotrope, from which it is not possible to extract the compound at the end of the reaction of formation of the adduct.

A further aim of the present invention is to carry out the reaction of formation of the compound that will form the adduct with the carbon allotrope on the allotrope itself but without the reagents that form the compound then being released from the adduct.

Another aim of the present invention is to use compounds, for forming the stable adduct with the carbon allotropes, that are derived from renewable sources without affecting the food cycle.

Finally, an aim of the present invention is to use, in the various preparatory steps, environmentally friendly solvents such as alcohols, ethers, esters and, ideally, water, and a further aim is to avoid any type of solvent.

These and other aims of the present invention are achieved with an adduct obtainable from:

a) the reaction product of a compound of formula (I)

in which X is selected from the group consisting of:

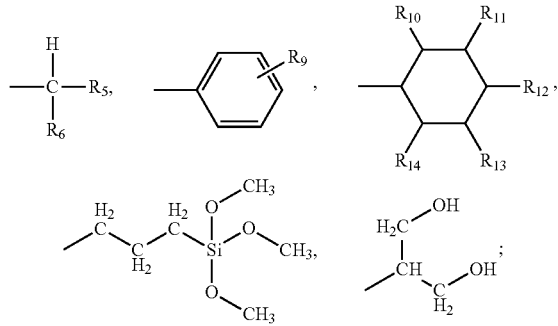

in which:

$R_5$ and $R_6$ are selected independently from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, or $R_5$ or $R_6$ are independently

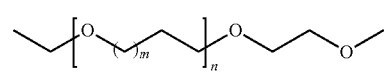

where m=0, 1,2 and n=1-30 where if only one of $R_5$ or $R_6$ is where m=0, 1, 2 and n=1-30
then the other is selected from the group consisting of: hydrogen, $C_1$-$C_{18}$ alkyl, linear or branched $C_2$-$C_{18}$ alkenyl or alkynyl;
or $R_5$ and/or $R_6$ are:

where n=0, 1, 2, 3
and $R_7$, $R_7'$, $R_7''$ are selected independently from the group consisting of: $C_1$-$C_4$ alkyl; $C_1$-$C_4$ oxygen-alkyl
or $R_5$ and/or $R_6$ are:

where n is an integer between 0 and 10 and $R_8$ and $R_8'$ are selected independently from the group consisting of: hydrogen, $C_1$-$C_4$ alkyl;
or $R_5$ and/or $R_6$ are:

where n is an integer between 1 and 10;
or $R_5$ and/or $R_6$ are:

and $R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alkyl-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, heteroaryl;

or $R_5$ and/or $R_6$ are:

and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl;
$R_9$ is selected from the group consisting of: hydrogen, alkyl, aryl, benzyl, amine, alkylamine, arylamine, benzylamine, aminoaryl;
$R_{10}$, $R_{11}$, $R_{12}$, $R_{13}$ and $R_{14}$ are selected independently from the group consisting of: hydrogen, $C_1$-$C_{18}$ alkyl, linear or branched $C_2$-$C_{18}$ alkenyl or alkynyl, 1-(4-aminocyclohexyl)methylene;
with a compound of formula (II)

(II)

in which n = 1-1000,
m = 1-1000
y = 0-1
z = 0-1 in which $R_{16}$ is selected from the group consisting of: hydrogen, methyl
and $R_{17}$ and $R_{18}$ are selected from the group consisting of: hydrogen, linear or branched $C_2$-$C_{30}$ alkyl or alkenyl or alkynyl, aryl, $C_2$-$C_{30}$ alkyl-aryl, linear or branched $C_2$-$C_{30}$ alkenyl-aryl, $C_2$-$C_{30}$ alkynyl-aryl, heteroaryl;
b) a carbon allotrope containing $sp^2$ hybridized carbon atoms;
c) an inorganic oxide-hydroxide.

Preferably the carbon allotrope or a derivative thereof is selected from the group consisting of graphene, nanographites consisting of few graphene layers (from a few units to several tens), graphite, fullerene, nanotoroids, nanocones, graphene nanoribbons, single-wall or multiwall carbon nanotubes, and carbon black, also called lampblack.

Even more preferably, the carbon allotrope or a derivative thereof is selected from the group consisting of carbon black, fullerene, single-wall or multiwall carbon nanotubes, graphene, graphite with a number of graphene layers between 2 and 10000.

The carbon allotrope may contain functional groups, selected from the group consisting of:
oxygenated functional groups, preferably hydroxyls, epoxides;
functional groups containing carbonyls, preferably aldehydes, ketones, carboxylic acids;
functional groups containing nitrogen atoms, preferably amines, amides, nitriles, diazonium salts, imines;
functional groups containing sulphur atoms, preferably sulphides, disulphides, mercaptans, sulphones, sulphinic and sulphonic groups.

In this way we have a wide range of carbon allotropes at our disposal.

Preferably the derivative of the carbon allotrope is graphite oxide or graphene oxide.

The inorganic oxide-hydroxide is a substance that contains both the oxide and the hydroxide as a functional group, and is preferably selected from the group consisting of: silica, layer silicates belonging to various groups, mixed oxides of aluminium and magnesium with a lamellar structure, alumina, aluminosilicates. Silica is particularly preferred.

With respect to silica, in particular, amorphous silica is preferred, which may be of natural origin, such as diatomite, or synthetic.

As synthetic silicas, the following may be used: precipitated silica, silica gel, pyrogenic silica, surface-treated silica.

With respect to the layered inorganic oxides-hydroxides, they may be cationic or neutral and belong to various groups, such as the groups of: serpentine-kaolin, talc-pyrophyllite, smectite, vermiculite, mica, chlorites, palygorskite and sepiolite, allophane and imogolite. Sepiolite is particularly preferred.

The layered inorganic oxides-hydroxides may be anionic: the hydrotalcites are of natural origin.

The silica used according to the present invention may be pyrogenic or, preferably, precipitated, with a BET surface area between 50 m$^2$/g and 500 m$^2$/g, preferably between 70 m$^2$/g and 200 m$^2$/g.

In the case of the layered oxides-hydroxides, the polar filler may be selected from layered materials that have a thickness of the single layer between 0.1 and 30 nm, preferably between 0.5 and 15 nm, even more preferably between 0.8 and 2 nm. These layered materials may be of natural or synthetic origin. These layered materials (known in the international scientific literature as clay) are a subset of the family of the layered oxides and are usually classified in three different categories, depending on the electric charge of the layer: (i) neutral layer, (ii) negatively charged layer, and (iii) positively charged layer.

The layered materials having a neutral layer or a negatively charged layer may belong to the group of serpentine and kaolin, to the group of talc and pyrophyllite, to the group of the smectites, such as montmorillonite, bentonite, beidellite, nontronite, volkonskoite, hectorite, fluorohectorite, Laponite, saponite, stevensite, sauconite, to the vermiculite group, to the mica group, such as celadonite, lepidolite, muscovite, phlogopite, to the chlorite group, to the group of palygorskite and sepiolite, to the group of allophane and imogolite. The layered materials having a positively charged layer may in particular be those of the hydrotalcite group. Montmorillonite is particularly preferred.

A further aspect of the present invention is to provide a process for preparing an adduct, comprising the reaction of a compound of formula (III)

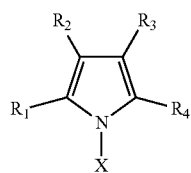
(III)

in which $R_1$, $R_2$, $R_3$, $R_4$ are selected independently from the group consisting of: hydrogen, $C_1$-$C_3$ alkyl, linear or branched $C_2$-$C_{18}$ alkenyl or alkynyl, aryl, linear or branched $C_1$-$C_{18}$ alkyl-aryl, linear or branched $C_2$-$C_{18}$ alkenyl-aryl, linear or branched $C_2$-$C_{18}$ alkynyl-aryl, heteroaryl, and X is selected from the group consisting of:

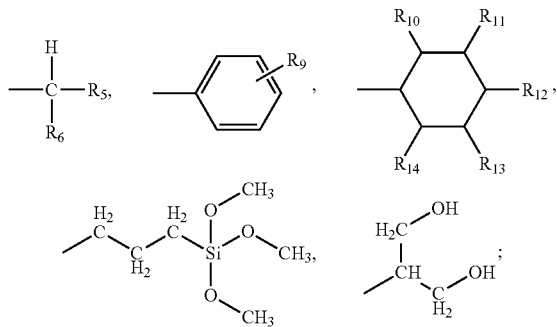

in which:

$R_5$ and $R_6$ are selected independently from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, or $R_5$ or $R_6$ are independently

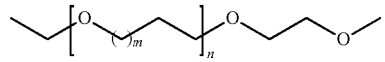

where m=0, 1, 2 and n=1-30 where if only one of $R_5$ or $R_6$ is

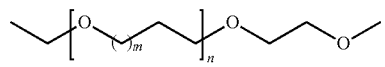

where m=0, 1, 2 and n=1-30 then the other is selected from the group consisting of: hydrogen, $C_1$-$C_{18}$ alkyl, linear or branched $C_2$-$C_{18}$ alkenyl or alkynyl;

or $R_5$ and/or $R_6$ are:

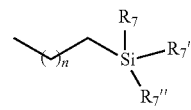

where n=0, 1, 2, 3 and $R_7$, $R_7'$, $R_7''$ are selected independently from the group consisting of: $C_1$-$C_4$ alkyl; $C_1$-$C_4$ oxygen-alkyl;

or $R_5$ and/or $R_6$ are:

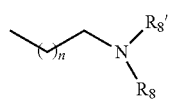

where n is an integer between 1 and 10 and $R_8$ and $R_8'$ are selected independently from the group consisting of: hydrogen, $C_1$-$C_4$ alkyl;

or $R_5$ and/or $R_6$ are:

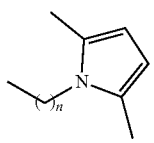

where n is an integer between 1 and 10;
or $R_5$ and/or $R_6$ are:

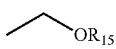

and $R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alkyl-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, heteroaryl;
or $R_5$ and/or $R_6$ are:

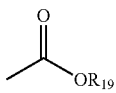

and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl;

$R_9$ is selected from the group consisting of: hydrogen, alkyl, aryl, benzyl, amine, alkylamine, arylamine, benzylamine, aminoaryl;

$R_{10}$, $R_{11}$, $R_{12}$, $R_{13}$ and $R_{14}$ are selected independently from the group consisting of: hydrogen, $C_1$-$C_{18}$ alkyl, linear or branched $C_2$-$C_{18}$ alkenyl or alkynyl, 1-(4-aminocyclohexyl)methylene;

with a carbon allotrope and an inorganic oxide-hydroxide by supplying thermal and/or mechanical energy and/or photon irradiation energy to the resultant mixture in the presence of oxygen ($O_2$).

Preferably the thermal energy is supplied at a temperature between 50° C. and 180° C. for a time between 15 and 360 minutes.

Preferably the mechanical energy is supplied for a time between 15 and 360 minutes.

Preferably the photon irradiation energy is supplied at a wavelength between 200 and 380 nm for a time between 30 and 180 minutes.

Preferably the compound of formula (III)
is obtained from the reaction of a compound of formula (I)

in which X is selected from the group consisting of:

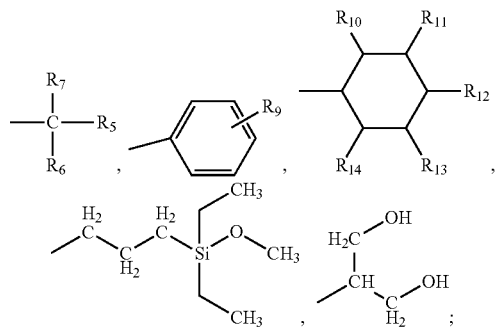

in which:

$R_5$ and $R_6$ are selected independently from the group consisting of: hydrogen, $C_1$-$C_{18}$ alkyl, linear or branched $C_2$-$C_{18}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl, or $R_5$ or $R_6$ are independently

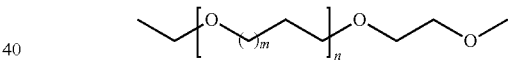

where m=0, 1,2 and n=1-30
where if only one of $R_5$ or $R_6$ is

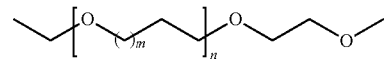

where m=0, 1, 2 and n=1-30
then the other is selected from the group consisting of: hydrogen, $C_1$-$C_{18}$ alkyl, linear or branched $C_2$-$C_{18}$ alkenyl or alkynyl;

or $R_5$ and/or $R_6$ are:

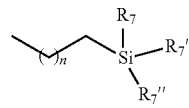

where n=0, 1, 2, 3
and $R_7$, $R_7'$, $R_7''$ are selected independently from the group consisting of: $C_1$-$C_4$ alkyl; $C_1$-$C_4$ oxygen-alkyl;

or $R_5$ and/or $R_6$ are:

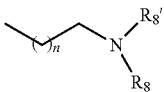

where n is an integer between 0 and 10
and $R_8$ and $R_8'$ are selected independently from the group consisting of: hydrogen, $C_1$-$C_4$ alkyl;
or $R_5$ and/or $R_6$ are:

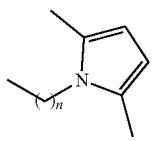

where n is an integer between 1 and 10;
or $R_5$ and/or $R_6$ are:

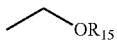

and $R_{15}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alkyl-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, heteroaryl;
or $R_5$ and/or $R_6$ are:

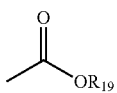

and $R_{19}$ is selected from the group consisting of: hydrogen, linear or branched $C_1$-$C_{22}$ alkyl, linear or branched $C_2$-$C_{22}$ alkenyl or alkynyl, aryl, linear or branched $C_1$-$C_{22}$ alkyl-aryl, linear or branched $C_2$-$C_{22}$ alkenyl-aryl, linear or branched $C_2$-$C_{22}$ alkynyl-aryl, heteroaryl;

$R_9$ is selected from the group consisting of: hydrogen, alkyl, aryl, benzyl, amine, alkylamine, arylamine, benzylamine, aminoaryl;

$R_{10}$, $R_{11}$, $R_{12}$, $R_{13}$ and $R_{14}$ are selected independently from the group consisting of: hydrogen, $C_1$-$C_{18}$ alkyl, linear or branched $C_2$-$C_{18}$ alkenyl or alkynyl, 1-(4-aminocyclohexyl)methylene;

with a compound of formula (II)

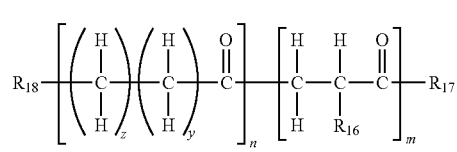

in which n = 1-1000,
m = 1-1000
y = 0-1
z = 0-1 in which $R_{16}$ is selected from the group consisting of: hydrogen, methyl;
and $R_{17}$ and $R_{18}$ are selected from the group consisting of: hydrogen, linear or branched $C_2$-$C_{30}$ alkyl or alkenyl or alkynyl, aryl, $C_2$-$C_{30}$ alkyl-aryl, linear or branched $C_2$-$C_{30}$ alkenyl-aryl, $C_2$-$C_{30}$ alkynyl-aryl, heteroaryl.

Some examples are given below relating to the conditions for preparing the adduct according to the present invention. For simplicity of explanation, these conditions will be indicated hereunder with the terms Type 1, Type 2, Type 3, Type 4, Type 5, Type 6, Type 7, Type 8, Type 9.

Type 1

According to a preferred embodiment, the adduct according to the present invention is obtained by a process comprising the following steps:
  i. providing a suspension of a carbon allotrope in a low-boiling liquid, preferably a protic or aprotic polar solvent, or non-polar promoting formation of the suspension by supplying energy, typically mechanical. The low-boiling solvent is preferably selected in such a way that it is a solvent of the compounds of formula (II) and of formula (III), which are then supplied as described in (ii);
  ii. adding a compound of formula (I), a compound of formula (II) and an inorganic oxide-hydroxide to suspension (i);
  iii. removing the low-boiling solvent, for example by evaporation at reduced pressure, obtaining a powder;
  iv. supplying thermal energy to the powder, with the following forms of energy: mechanical and/or thermal and/or photon irradiation energy.

Type 2

According to another preferred embodiment, the adduct according to the present invention is obtained by a process comprising the following steps:
  i. providing a solution of a compound of formula (I) and of a compound of formula (II) in a protic or aprotic polar solvent, or a non-polar solvent;
  ii. providing a suspension of the carbon allotrope in a protic or aprotic polar solvent or in a non-polar solvent, said solvents being used for preparing the solution as in step i.;
  iii. adding an inorganic oxide-hydroxide to the suspension as in step
  (ii) and preparing a dispersion of the allotrope and of silica;
  iv. mixing the solution prepared in step (i) and the dispersion prepared in step (iii);
  v. removing the solvent;
  vi. supplying thermal energy and/or mechanical energy and/or photon irradiation energy to the mixture obtained.

Type 3

According to another preferred embodiment, the adduct according to the present invention is obtained by a process comprising the following steps:
i. providing a solution of a compound of formula (I) and of a compound of formula (II) in a protic or aprotic polar solvent, or a non-polar solvent;
ii. adding a carbon allotrope and an inorganic oxide-hydroxide;
iii. removing the solvent;
iv. supplying thermal energy and/or mechanical energy and/or photon irradiation energy to the mixture obtained.

Type 4

According to another preferred embodiment, the adduct according to the present invention is obtained by a process comprising the following steps:
i. mixing a compound of formula (I), a compound of formula (II), a carbon allotrope and an inorganic oxide-hydroxide in the solid state;
ii. supplying thermal energy and/or mechanical energy and/or photon irradiation energy to the mixture obtained.

Type 5

According to another preferred embodiment, the adduct according to the present invention is obtained by a process comprising the following steps:
i. providing a mixture of a compound of formula (I), of a compound of formula (II) and of an inorganic oxide-hydroxide in a protic or aprotic polar solvent, or a non-polar solvent;
ii. removing the solvent, obtaining a powder;
iii. the powder obtained may be processed as indicated in step (iv) or thermal energy and/or mechanical energy and/or photon irradiation energy may be supplied to this powder;
iv. mixing the mixture obtained in step (ii) with a carbon allotrope, in the solid state, in the absence of a solvent, obtaining a mixture in the solid state, preferably a powder;
v. supplying thermal energy and/or mechanical energy and/or photon irradiation energy to the mixture obtained.

Type 6

According to another preferred embodiment, the adduct according to the present invention is obtained by a process comprising the following steps:
i. providing a mixture of a compound of formula (I), of a compound of formula (II) and of an inorganic oxide-hydroxide, in the solid state, preferably obtaining a powder;
ii. the powder obtained may be processed as indicated in step (iii) or thermal energy and/or mechanical energy and/or photon irradiation energy may be supplied to this powder;
iii. mixing the mixture obtained in step (i) or in step (ii) with a carbon allotrope, in the solid state, in the absence of a solvent, obtaining a mixture in the solid state, preferably a powder;
iv. supplying thermal energy and/or mechanical energy and/or photon irradiation energy to the mixture obtained.

Type 7

According to another preferred embodiment, the mixture of compounds (a), (b), (c) and (d) is obtained by a process comprising the following steps:
i. providing a mixture of a compound of formula (I), of a compound of formula (II) and of an inorganic oxide-hydroxide, in the solid state, preferably obtaining a powder;
ii. the powder obtained may be processed as indicated in step (iii) or thermal energy and/or mechanical energy and/or photon irradiation energy may be supplied to this powder;
iii. mixing the mixture obtained in step (i) or in step (ii) with a carbon allotrope, in an amorphous polymer or a polymer melt, obtaining a mixture in the solid state, a polymer composite. Supplying energy, preferably thermal and/or mechanical, during mixing. Machines that can be used for mixing are internal mixers such as Brabender or Banbury mixers, or counter-rotating or, preferably, co-rotating single-screw or twin-screw extruders.

Type 8

According to another preferred embodiment, the adduct according to the present invention is obtained by a process comprising the following steps:
i. providing a mixture of a compound of formula (I), of a compound of formula (II), of an inorganic oxide-hydroxide and of a carbon allotrope in an amorphous polymer or a polymer melt, obtaining a mixture in the solid state, a polymer composite. Supplying energy, preferably thermal and/or mechanical, during mixing. Machines that can be used for mixing are internal mixers such as Brabender or Banbury mixers or counter-rotating or, preferably, co-rotating single-screw or twin-screw extruders.

Type 9

According to another preferred embodiment, the adduct according to the present invention is obtained by a process comprising the following steps:
i. providing a suspension of a carbon allotrope in a low-boiling liquid, promoting formation of the suspension by supplying energy, typically mechanical;
ii. adding a compound of formula (III) and an inorganic oxide-hydroxide;
iii. removing the solvent, for example by evaporation at reduced pressure, obtaining a powder;
iv. supplying thermal energy and/or mechanical energy and/or photon irradiation energy to the powder obtained in step (iii).

Type 9b

According to another preferred embodiment, the adduct according to the present invention is obtained by a process comprising the following steps:
i. providing a solution of a compound of formula (III) and a suspension of a carbon allotrope and of an inorganic oxide-hydroxide in a low-boiling liquid, promoting formation of the suspension by supplying energy, typically mechanical;
ii. removing the solvent, for example by evaporation at reduced pressure, obtaining a powder;
iii. supplying thermal energy and/or mechanical energy and/or photon irradiation energy to the powder obtained in step (iii).

Type 9c

According to another preferred embodiment, the adduct according to the present invention is obtained by a process comprising the following steps:
i. providing a mixture, in the solid state, of a compound of formula (III), a carbon allotrope and of an inorganic oxide-hydroxide;

ii. supplying thermal energy and/or mechanical energy and/or photon irradiation energy to the powder obtained in step (iii).

According to the present invention, the inorganic oxide-hydroxide, and in particular silica, perform a triple role:

(i) to promote formation of the pyrrole compound during the reaction between a primary amine and a 1,4-dicarbonyl compound, wherein there is addition of the nitrogen doublet onto the carbonyl carbon with consequent formation of a covalent bond. For the species to be able to progress to pyrrole, and then form an aromatic compound, it is generally necessary to supply energy to the system or add a catalytic species. The role of the organic oxides-hydroxides during the reaction is to allow formation of the heterocycle even at room temperature.

(ii) to interact with the polar groups of the oxidized pyrrole compound. It will be recalled that the oxide-hydroxide is able to function as a donor or acceptor of hydrogen bonds and so is able to interact with the polar groups (aldehyde, amide) that form by the oxidation of the pyrrole compound.

(iii) to prevent extraction of the oxidized species and of the pyrroles from the adduct. If there is a sufficient amount of silica in the adduct, there is no extraction of organic substances from said adduct. Therefore its role is to prevent extractability of the organic substances.

According to the present description, for formation of the adduct to take place as claimed, it is necessary to carry out the reactions in the presence of oxygen. Oxygen and high temperature are necessary conditions for formation of the adducts. The role of oxygen is therefore that of oxidizing agent of the pyrrole compound.

The oxygen necessary for carrying out the reaction may come directly from the environment in which the reaction is carried out, and therefore from the air, or may advantageously be derived from oxygen donating compounds that are added to the reaction products so as to supply a certain constant amount of oxygen to said reaction. Some examples of oxygen donors according to the present invention are: $H_2O_2$, $MnO_2$, $KMnO_4$, $HNO_3$, NaClO (sodium hypochlorite), $NaCl_2$ (sodium chlorite), $H_2SO_4/HNO_3$ (mixture of sulphuric and nitric acid), $NaIO_4$ (sodium metaperiodate), $HIO_4$, $OsO_4$, $Pb(C_2H_3O_2)_4$ (lead tetraacetate), $HNO_3/HNO_2$, $CO_2$, CO, dicumyl peroxide, $RuO_2$, $RuO_4$, $SeO_2$, $O_3$, Dess-Martin periodinane, peroxyacetic acid, iodosobenzoic acid (IBX), nicotinamide-adenine dinucleotide (NAD+), enzymes (laccase, oxidase).

According to the present invention, the term "moles of carbon allotrope" means the moles of benzene ring regarded as the basic constituent repeating unit of the carbon allotrope containing $sp^2$ hybridized carbon atoms.

In order to obtain a stable adduct that satisfies the characteristics listed above, the carbon allotrope is in a molar ratio between 100:1 and 1:50 relative to the compounds of formula (I) or (II), preferably in a molar ratio between 50:1 and 1:20.

According to one aspect of the invention, the carbon allotrope is in a molar ratio between 10:1 and 1:5 relative to the compounds of formula (I) or (II), even more preferably in a molar ratio between 4:1 and 1:2.

According to the present invention, the terms "carbon allotrope" and "carbon filler" are used interchangeably.

According to the present invention, the term adduct means a compound obtained by an addition reaction; more specifically, adducts are those particular addition compounds whose components, bound more or less unstably, preserve their individuality in some way.

According to the present invention, the term solvent refers to the compounds of formula (I), of formula (II), of formula (III) and obviously not to the carbon allotrope, for which the solvent only performs the task of dispersant. Preferably the solvent should be environmentally friendly.

Generally, owing to the chemical nature of carbon, it is rather difficult to disperse carbon fillers in liquid matrices. The use of ultrasound makes it possible to effect dispersion in reasonable times and improve the homogeneity of the dispersion of the carbon filler (even a few seconds). Moreover, the use of sonication makes it possible to separate, to a varying extent, the carbon nanofillers into the basic units. For example, it is possible to promote separation of the carbon nanotubes into the individual tubes from the tangle in which they are intertwined with other tubes. It is advisable to use low-power sonicators, of the classical ultrasonic bath type, to avoid breaking the nanotubes themselves, and reducing their length. With suitable solvents it is also possible to effect partial exfoliation of a graphite having a varying initial number of stacked layers. Graphites with a small number of stacked layers have nanometric dimensions and are called nanographites. It is therefore preferred to contact the nanofiller with a liquid in a preliminary step, so as to obtain, by sonication, and depending on the nanofiller, either so-called untangling of the carbon nanotubes, or more or less pronounced exfoliation of the graphite or nanographite. This procedure leads to improvement of contact between the nanofiller and the serinol derivative containing a pyrrole ring, also leading to increase in the exposed area of the nanofiller.

According to the present invention the term "sonochemistry" indicates the physicochemical discipline that studies the chemical reactions that occur in a solution irradiated with ultrasound. This irradiation gives rise, for a field intensity above a certain threshold value, to a phenomenon of cavitation in the solution. The gas microcavities (bubbles) present in the solution, subjected to successive expansion and contraction induced by the oscillating field of sound pressure, increase in size and then implode, producing zones with extremely high temperature and pressure. In these extreme conditions, chemical reactions may occur that are of considerable interest in the field of the synthesis of organic substances, polymerization processes, and degradation of toxic and harmful substances. By employing sonication techniques it is also possible to obtain amorphous materials which, without the extreme conditions typical of sonication, would have a natural tendency to crystallize.

The method of removing the solvent from the mixture obtained may take place by any suitable method for removal of solvents, for example vacuum evaporation, spray drying, etc.

The mixture obtained after removing the solvent from the mixture containing the carbon allotrope, the inorganic oxide-hydroxide and the compound of formula (I) with the compound of formula (II) or the compound of formula (III) typically undergoes a further step in which energy is transferred to the composition.

The forms of energy that may be transferred to the composition to allow formation of the adduct, are:
mechanical energy
thermal energy
photons Mechanical Energy The mixture that is obtained between the nanofiller and at least one derivative containing a pyrrole ring, obtained by the process described above in steps a-c, is treated by a mechanical process.

The mechanical treatment consists of putting the powder obtained in a jar equipped with stainless-steel balls. Once closed, the jar is put in a planetary mixer and is rotated at a speed from 200 to 500 rpm for times from 1 to 360 minutes. The powder is discharged immediately thereafter.

The mechanical treatment referred to is used both for inducing disorder (exfoliation in the case of graphite) in order to obtain better distribution on the nanofiller, and for inducing development of much more stable interaction.

This is possible as it is known in chemistry that it is possible to induce chemical reactions of dry mixtures by subjecting them to mechanical forces. Mechanochemistry is a little-known branch of chemistry that is of considerable interest on account of its environmentally friendly character. A mechanochemical process can be initiated simply using pestle and mortar or using more unwieldy systems but with simple operation such as ball mills, used in the pharmaceutical industry and the food industry.

So-called planetary ball mills have cylindrical reactors, jars, held in a vertical position on a rotating platform. In mills with jars containing balls, use is made of the collisions between the balls, which typically number between 5 and 50. The efficiency with which a given mill operates in relation to a given mechanochemical transformation is closely linked to the frequency of the collisions between the balls and the inside wall of the jar and to the mechanical energy transferred. These quantities depend in their turn on the dynamics of the balls, their size and how many there are, on the frequency of oscillation, or work, of the mill, and on the total amount of powder in the reactor.

Thermal Energy

The mixture that is obtained between the nanofiller and at least one derivative containing a pyrrole ring, obtained by the process described above in steps a-c, is treated by a thermal process.

The thermal treatment consists of putting the powder obtained in a reaction flask equipped with a condenser or in a sealed ampoule. Once the reactor has been set up on a hot plate, the reaction is carried out at temperatures from 130° C. to 180° C. Heating is maintained from a minimum of 2 hours to 12. The thermal treatment induces the formation of stable interactions.

Photons

The mixture that is obtained between the nanofiller and at least one derivative containing a pyrrole ring, obtained by the process described above in steps a-c, is treated by an irradiation process using a lamp with a suitable wavelength.

The treatment with photons consists of putting the powder obtained in a laboratory crystallizer forming a thin layer or putting the powder in a sealed quartz ampoule. Once the reactor is set up inside a dark chamber equipped with a low-pressure mercury lamp at 254 nm (or using a Rayonet® reactor equipped with the same type of lamp) the mixture is irradiated for times varying from 30 to 180 minutes. After this time the mixture is discharged and analysed.

With an adduct according to the present invention it is possible to obtain stable suspensions of carbon nanofillers both in aqueous media and in other substrates such as polymer blends or rubber, so as to obtain homogeneous products that have the particular characteristics of the carbon nanofillers, for example high mechanical properties, high electrical conductivity, resistance to high temperatures, and flame-retardant properties.

With an adduct according to the present invention it is also possible to obtain uniform, continuous layers of carbon black fillers on various substrates in order to obtain highly conductive surfaces.

Without being bound to particular theories or interpretations of possible reaction mechanisms, it is thought that the amine and the diketone, in contact with the $sp^2$ carbon allotrope, form a pyrrole compound. The pyrrole compound, thus formed or already pre-formed, at high temperature and in the presence of the $sp^2$ carbon allotrope, gives rise to oxidation reactions. Unsaturated substances may thus form, with activated double bonds that can give reactions of cycloaddition with the carbon allotrope. Silica may promote the reaction of formation of the pyrrole compound and, by reacting with the polar groups of the oxidized pyrrole compound, prevents extraction thereof from the adduct.

The adduct according to the present invention will be better illustrated by the examples given hereunder, which illustrate the operating steps of the process of preparation from said adduct.

EXAMPLES

The adducts obtained by the examples presented below were analysed as follows:

infrared spectroscopy (FT-IR), using a KBr pellet: adduct/KBr weight ratios of 1:500 were used, and about 80 mg of mixture for forming the pellet. The pellet was analysed with a Fourier transform IR spectrophotometer (Varian 640-IR FT-IR spectrometer with ATR option). The samples were irradiated in a range between 2.5 and 20 μm (or between 4000 and 500 $cm^{-1}$).

UV spectroscopy: the suspensions of adduct (3 mL) were placed, using a Pasteur pipette, in quartz cuvettes with a 1 cm optical path (volume 1 or 3 mL) and were analysed using a UV-Vis spectrophotometer. The instrument is zeroed with the pure solvent and a UV spectrum is recorded from 200 to 340 nm. A blank of the solvent used was recorded. The UV-visible spectrum gave the intensity of absorption as a function of the wavelength of the radiation between 200 and 750 nm.

NMR (nuclear magnetic resonance): This technique was used for confirming the structure of the pyrrole compounds. $^1H$ NMR spectra were recorded at a temperature of 27° C. using a Bruker AV 400 spectrometer operating at 400 MHz (Bruker, Rheinstetten, Germany). The solvents used for performing the analysis were deuterated, deuterated chloroform ($CDCl_3$) being used in particular.

Extraction Test

This test is intended to verify the stability of the interaction between the carbon allotrope, the organic oxide-hydroxide and the pyrrole compound.

Procedure:

Acetone (100 mL) is poured into a 250-mL single-neck flask equipped with a Soxhlet extractor. A filtering crucible containing powdered adduct (10 g) is put inside the Soxhlet extractor. Continuous extraction is performed at the boiling point of acetone (56° C.) for 12 hours. After this time, the powder is recovered from the extraction crucible and is dried in a stove. An aliquot of the acetone is injected into a gas chromatograph combined with a mass spectrometer Agilent 5973 Network Mass Selective Detector with 6890 Series GC System.

Test of Stability of the Suspension

This test is intended to verify the capacity of the ternary system consisting of the carbon allotrope, the inorganic oxide-hydroxide and the pyrrole compound, for forming suspensions that are stable over time. The stability in solvents was evaluated in a polar medium, water, and in a non-polar medium, toluene.

Procedure, Stability in Water:

10 mg of powdered adduct was put in a 10-mL flask, and distilled water (10 mL) was added. The mixture was sonicated in a 2-litre ultrasonic bath, with power of 260 W, for 20 minutes.

The suspensions of adduct (3 mL) at a concentration of 1 mg/mL were transferred, using a Pasteur pipette, to quartz cuvettes with a 1 cm optical path (volume 1 or 3 mL) and were analysed using a UV-Vis spectrophotometer. The instrument was zeroed beforehand with pure solvent, recording a UV spectrum (200-340 nm). The UV-visible spectrum gave the intensity of absorption as a function of the wavelength of the radiation between 200 and 750 nm.

To evaluate the stability over time of the suspensions obtained, measurement of UV-Vis absorption was then repeated a week later.

Procedure, Stability in Toluene:

10 mg of powdered adduct was put in a 10-mL flask, and toluene (10 mL) was added. The mixture was sonicated in a 2-litre ultrasonic bath, with power of 260 W for 20 minutes.

The suspensions of adduct (3 mL) at a concentration of 1 mg/mL were transferred, using a Pasteur pipette, to quartz cuvettes with a 1 cm optical path (volume 1 or 3 mL) and were analysed using a UV-Vis spectrophotometer. The instrument was zeroed beforehand with pure solvent, recording a UV spectrum (200-340 nm). The UV-visible spectrum gave the intensity of absorption as a function of the wavelength of the radiation between 200 and 750 nm.

To evaluate the stability over time of the suspensions obtained, measurement of UV-Vis absorption was then repeated a week later.

Tests of Preparation of the Adducts

Tables 1A and 1B present the tests carried out for preparation of the adducts. The ingredients for preparing the adducts are: amine (A), diketone (B), carbon allotrope (C), inorganic oxide-hydroxide (D), pyrrole compound (P).

TABLE 1A

Tests of preparation of the adducts

| Ex. | Substances mixed (A) Amine | (B) Diketone | Pyrrole compound (P) | Carbon allotrope (C) | Inorganic oxide hydroxide (D) |
|---|---|---|---|---|---|
| 1 inv | Serinol | 2,5-ED | 0 | CB N326 | SiO$_2$ |
| 2 inv | Serinol | 2,5-ED | 0 | CB N326 | SiO$_2$ |
| 3 inv | Serinol | 2,5-ED | 0 | CB N326 | SiO$_2$ |
| 4 inv | Serinol | 2,5-ED | 0 | CB N326 | Mt |
| 5 inv | Hexanamine | 2,5-ED | 0 | CB N326 | SiO$_2$ |
| 6 inv | APTES | 2,5-ED | 0 | CB N326 | SiO$_2$ |
| 7 cmp | Serinol | 2,5-ED | 0 | = | SiO$_2$ |
| 8 cmp | = | 2,5-ED | 0 | CB N326 | SiO$_2$ |
| 9 cmp | Serinol | = | 0 | CB N326 | SiO$_2$ |
| 10 cmp | Serinol | 2,5-ED | 0 | CB N326 | = |
| 11 inv | = | = | Hexyl pyrrole | CB N326 | SiO$_2$ |
| 12 inv | = | = | Hexyl pyrrole | graphite | SiO$_2$ |
| 13 inv | = | = | Trimethyl pyrrole | CB N326 | SiO$_2$ |
| 14 inv | = | = | Trimethyl pyrrole | graphite | SiO$_2$ |
| 15 inv | Serinol | 2,5-ED | 0 | CB N326 | SiO$_2$ |
| 16 inv | Hexanamine | 2,5-ED | 0 | CB N326 | SiO$_2$ |
| 17 inv | Serinol | 2,5-ED | 0 | CB N326 | SiO$_2$ |
| 18 inv | Hexanamine | 2,5-ED | 0 | CB N326 | SiO$_2$ |
| 19 inv | Serinol | 2,5-ED | 0 | CB N326 | SiO$_2$ |
| 20 inv | Hexanamine | 2,5-ED | 0 | CB N326 | SiO$_2$ |

2,5-ED = 2,5-hexanedione;
SiO$_2$ = Zeosil 1165 MP (Rhodia)

TABLE 1B

Tests of preparation of the adducts

| Ex. | Molar ratio A/B | Molar ratio (A)/(C) | Weight ratio (A + B)/(C) | Molar ratio (P)/(C) | Weight ratio (P)/(C) | Weight ratio (C)/(D) | Proc. |
|---|---|---|---|---|---|---|---|
| 1 inv | 1:1 | 1:10 | 1/3.51 | = | = | 1:1 | 1 |
| 2 inv | 1:1 | 1:10 | 1/3.51 | = | = | 2:1 | 1 |
| 3 inv | 1:1 | 1:10 | 1/3.51 | = | = | 4:1 | 1 |
| 4 inv | 1:1 | 1:10 | 1/3.51 | = | = | 1:1 | 1 |
| 5 inv | 1:1 | 1:10 | 1/2.1 | = | = | 1:1 | 1 |
| 6 inv | 1:1 | 1:10 | 1/1.35 | = | = | 1:1 | 1 |
| 7 cmp | 1:1 | = | | = | = | 0 | |
| 8 cmp | 0 | 0 | 1/6.31 | | | 1:1 | |
| 9 cmp | = | 1:10 | 1/7.91 | = | = | 1:1 | |
| 10 cmp | 1:1 | 1:10 | 1/3.51 | = | = | = | 1 |
| 11 inv | = | 0 | = | 1:10 | 1:4.03 | 1:1 | 9 |
| 12 inv | = | 0 | = | 1:10 | 1:4.03 | 1:1 | 9 |
| 13 inv | = | 0 | = | 1:10 | 1:6.60 | 1:1 | 9 |
| 14 inv | = | 0 | = | 1:10 | 1:6.60 | 1:1 | 9 |
| 15 inv | 1:1 | 1:10 | 1/3.51 | = | = | 1:1 | 2 |
| 16 inv | 1:1 | 1:10 | 1/2.1 | = | = | 1:1 | 2 |
| 17 inv | 1:1 | 1:10 | 1/3.51 | = | = | 1:1 | 5 |
| 18 inv | 1:1 | 1:10 | 1/2.1 | = | = | 1:1 | 5 |
| 19 inv | 1:1 | 1:10 | 1/3.51 | = | = | 1:1 | 6 |
| 20 inv | 1:1 | 1:10 | 1/2.1 | = | = | 1:1 | 6 |

The adducts according to the present invention were prepared starting from:

(i) amine, diketone, carbon allotrope, inorganic oxide-hydroxide: examples 1, 2, 3, 4, 5, 6, 15, 16, 17, 18, 19, 20;

(ii) pyrrole compound, carbon allotrope, inorganic oxide-hydroxide: examples 11, 12, 13, 14.

In examples 1, 2, 3, 4, 5 and 6, the carbon allotrope is firstly pre-dispersed in an environmentally friendly low-boiling solvent such as acetone and then the amine, diketone and silica are added to this dispersion. The solvent is then removed and the powder obtained is then heated. Further details are given in the description of the examples.

In examples 1, 2 and 3, the adduct is formed from serinol, 2,5-hexanedione, carbon black and silica. The molar ratio between serinol and hexanedione (molar ratio A/B) is the stoichiometric ratio for the Paal-Knorr reaction. The molar ratio between serinol and the carbon allotrope (molar ratio A/C) is equal to 1/10. This molar ratio indicates the ratio between serinol and the benzene ring, regarded as the constituent unit of the allotrope. It is thus a calculated ratio. Table 1 also gives the weight ratio between the sum of amine and diketone and the carbon allotrope. This is a primary experimental value, since all the substances are weighed.

Table 1 also gives the weight ratio between the carbon allotrope and silica. Silica in fact has a dual function: it performs the role of catalyst for the reaction of the amine with the diketone and thus allows formation of the pyrrole compound even at low temperature and prevents extractability of the organic substances that form the adduct, from said adduct.

In example 4, the inorganic oxide-hydroxide consists of montmorillonite. The other components of the adduct remain unchanged. A 1:1 ratio of carbon black to montmorillonite was adopted.

In example 5, hexanamine was used as the amine. The different value of the weight ratio (A+B)/(C) is only due to the different molar mass of the hexanamine.

In example 6, (3-aminopropyl)triethoxysilane was used as the amine. In this case too, the different value of the weight ratio (A+B)/(C) is only due to the different molar mass of the silane, relative to the amines used in the previous examples. A 1:1 ratio of carbon black to silica was adopted.

Examples 7, 8, 9 and 10 constitute comparative examples of the present invention. Each of these lacks one component of the adduct of the present invention. In example 7, no carbon allotrope was used. In example 8, no amine was used, in example 9, no diketone was used, and in example 10, no inorganic oxide-hydroxide was used. Mixing of the components was carried out according to the same experimental procedure as in examples 1-6, obviously taking into account the absence of one of the components of the adduct.

In examples 11, 12, 13 and 14 of the present invention, the adduct is formed by bringing a pyrrole compound, a carbon allotrope and silica into contact. The experimental procedure is the same as that followed for examples 1-6, with the substantial difference that instead of adding amine, diketone and silica to the suspension of the allotrope in acetone, the pyrrole compound and silica are added. In examples 11 and 12, the pyrrole compound used was a compound called N-hexylpyrrole, prepared by reaction of hexanamine with 2,5-diketone. In examples 13 and 14, trimethyl pyrrole was used—a compound that is available commercially. In examples 11 and 13, the carbon allotrope used was carbon black. In examples 12 and 14, the carbon allotrope used was a high surface area graphite, of nanometric dimensions.

In examples 15, 16, 17, 18, 19, and 20, amine, diketone, carbon allotrope and inorganic oxide-hydroxide were used for preparing the adduct according to the present invention. In all these examples the carbon allotrope was carbon black, and the inorganic oxide-hydroxide was silica. In examples 15, 17 and 19 the amine was serinol, in examples 16, 18 and 20, the amine was hexanamine. The ratios of the components adopted are, for serinol, equal in examples 15, 17 and 19 and are also equal to those adopted in example 1. The ratios of the components adopted are, for hexanamine, equal in examples 16, 18 and 20 and are also equal to those adopted in example 5. In examples 15-20, the experimental procedures for preparing the adduct were modified relative to example 1 and example 5. In examples 15 and 16, the amine and the diketone were premixed in the same solvent used for preparing the suspension of the allotrope. Both silica and the solution of amine and diketone in acetone were added to the suspension of the allotrope in acetone. From here, the procedure was the same as that adopted for example 1 and example 5.

In examples 17 and 18, the amine and the diketone were premixed with silica in an environmentally friendly low-boiling solvent such as acetone. This solvent was then removed and a powder was obtained, which was then heated. The powder was then mixed in the solid state with the carbon allotrope. From here, the procedure is the same as that adopted for examples 1 and 5.

In examples 19 and 20, the amine and the diketone were premixed with silica in the solid state. The powder was heated and was then mixed in the solid state with the carbon allotrope. From here, the procedure is the same as that adopted for examples 1 and 5.

Example 1

Invention

Adduct of 2-amino-1,3-propanediol (serinol), 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The serinol used is Bracco and the 2,5-hexanedione was acquired from Aldrich.

A 100-mL single-neck flask is charged with 2.5 g of carbon black and 15 mL of acetone. The suspension is sonicated in an ultrasonic bath for 15 minutes. After this time, the following are added successively: 0.316 g of serinol, 0.396 g of 2,5-hexanedione and silica (2.5 g). The resultant suspension is sonicated for 15 minutes. The solvent is removed at reduced pressure. A powder is obtained, consisting of serinol and 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

A suspension in water was prepared with the sample of treated carbon black after heating at 180° C. for 2 hours. The suspension, having a concentration equal to 1 mg/mL, was sonicated for 10 minutes and was analysed by ultraviolet (UV) spectroscopy. UV spectra were recorded immediately after sonication and after 24 hours and they showed the same absorbance.

Example 2

Invention

Adduct of 2-amino-1,3-propanediol (serinol), 2,5-hexanedione with carbon black and silica (carbon black/silica ratios 2/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The serinol used is Bracco and the 2,5-hexanedione was acquired from Aldrich.

A 100-mL single-neck flask is charged with 3.33 g of carbon black and 15 mL of acetone. The suspension is sonicated in an ultrasonic bath for 15 minutes. After this time, the following are added successively: 0.421 g of serinol, 0.527 g of 2,5-hexanedione and silica (1.67 g). The resultant suspension is sonicated for 15 minutes. The solvent is removed at reduced pressure. A powder is obtained, consisting of serinol and 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

A suspension in water was prepared with the sample of treated carbon black after heating at 180° C. for 2 hours. The suspension, having a concentration equal to 1 mg/mL, was sonicated for 10 minutes and was analysed by ultraviolet (UV) spectroscopy. UV spectra were recorded immediately after sonication and after 24 hours and they showed the same absorbance.

Example 3

Invention

Adduct of 2-amino-1,3-propanediol (serinol), 2,5-hexanedione with carbon black and silica (carbon black/silica ratios 4/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The serinol used is Bracco and the 2,5-hexanedione was acquired from Aldrich.

A 100-mL single-neck flask is charged with 4 g of carbon black and 15 mL of acetone. The suspension is sonicated in an ultrasonic bath for 15 minutes. After this time, the following are added successively: 0.506 g of serinol, 0.630 g of 2,5-hexanedione and silica (1 g). The resultant suspension is sonicated for 15 minutes. The solvent is removed at reduced pressure. A powder is obtained, consisting of serinol and 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

Example 4

Invention

In this example, Dellite was used instead of silica.

Adduct of 2-amino-1,3-propanediol (serinol), 2,5-hexanedione with carbon black and Dellite (carbon black/Dellite ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The serinol is Bracco. The 2,5-hexanedione is from Aldrich.

A 100-mL single-neck flask is charged with 2.5 g of carbon black and 15 mL of acetone. The suspension is sonicated in an ultrasonic bath for 15 minutes. After this time, the following are added successively: 0.316 g of serinol, 0.396 g of 2,5-hexanedione and Dellite (2.5 g). The resultant suspension is mixed and sonicated for 15 minutes. The solvent is removed at reduced pressure. A powder is obtained, consisting of serinol and 2,5-hexanedione absorbed on the mixture of carbon black and Dellite.

The powder is put in a 100-mL flask equipped with a magnetic stirrer and is heated at a temperature of 180° C. for 2 hours. After this time, the powder is cooled to 25° C.

Example 5

Invention

Adduct of hexanamine, 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The hexanamine and 2,5-hexanedione were acquired from Aldrich.

A 100-mL single-neck flask is charged with 2.5 g of carbon black and 15 mL of acetone. The suspension is sonicated in an ultrasonic bath for 15 minutes. After this time, the following are added successively: 0.558 g of hexanamine, 0.630 g of 2,5-hexanedione and silica (2.5 g). The resultant suspension is sonicated for 15 minutes. The solvent is removed at reduced pressure. A powder is obtained, consisting of hexanamine and 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

Example 6

Invention

Adduct of 3-aminopropyltriethoxysilane, 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The 3-am inopropyltriethoxysilane and 2,5-hexanedione were acquired from Aldrich.

A 100-mL single-neck flask is charged with 2.5 g of carbon black and 15 mL of acetone. The suspension is sonicated in an ultrasonic bath for 15 minutes. After this time, the following are added successively: 1.22 g of 3-aminopropyltriethoxysilane, 0.630 g of 2,5-hexanedione and silica (2.5 g). The resultant suspension is sonicated for 15 minutes. The solvent is removed at reduced pressure. A powder is obtained, consisting of 3-aminopropyltriethoxysilane and 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

Example 7

Comparison

Only silica was used in this example (no carbon allotrope).

Adduct of 2-amino-1,3-propanediol (serinol), 2,5-hexanedione with silica. Synthesis of 2-(2,5-dimethyl-1H-pyrrol-1-yl)propane-1,3-diol.

The silica used is Zeosil 1165 MP (Rhodia). The serinol is Bracco and the 2,5-hexanedione is from Aldrich.

A 50-mL single-neck flask is charged with 1 g of silica and successively 0.082 g of serinol and 0.104 g of 2,5-hexanedione. The mixture is first sonicated (15 minutes) and then is stirred at 25° C. for a week. After this time a portion is removed, filtered on a Büchner using $D_2O$ and analysed by $^1H$ NMR analysis. The spectrum revealed the presence of 2-(2,5-dimethyl-1H-pyrrol-1-yl)propane-1,3-diol.

Example 8

Comparison

Silica, carbon black and the dicarbonyl compound were used in this example (no primary amine).

Adduct of 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 m$^2$/g (determined by nitrogen absorption), absorption of DBP equal to 85 mL/100 g. The silica used is Zeosil 1165 MP (Rhodia). The 2,5-hexanedione was acquired from Aldrich.

A 100-mL single-neck flask is charged with 2.5 g of carbon black and 15 mL of acetone. The suspension is sonicated in an ultrasonic bath for 15 minutes. After this time, the following are added successively: 0.396 g of 2,5-hexanedione and silica (2.5 g). The resultant suspension is sonicated for 15 minutes. The solvent is removed at reduced pressure. A powder is obtained, consisting of 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

Example 9

Comparison

Silica, carbon black and a primary amine (serinol) were used in this example (no dicarbonyl compound).

Adduct of serinol with carbon black and silica (carbon black/silica ratios 1/1 by weight).

The carbon black used is Carbon Black N326 (CB) (Cabot), with the following characteristics: 30 nm average diameter of the spherical particles, surface area equal to 77 m$^2$/g (determined by nitrogen absorption), absorption of DBP equal to 85 mL/100 g. The silica used is Zeosil 1165 MP (Rhodia). The serinol used is Bracco.

A 100-mL single-neck flask is charged with 2.5 g of carbon black and 15 mL of acetone. The suspension is sonicated in an ultrasonic bath for 15 minutes. After this time, the following are added successively: 0.316 g of serinol and silica (2.5 g). The resultant suspension is sonicated for 15 minutes. The solvent is removed at reduced pressure. A powder is obtained, consisting of serinol absorbed on the mixture of carbon black and silica.

The powder is put in a 100-mL flask equipped with a magnetic stirrer and is heated at a temperature of 180° C. for 2 hours. After this time, the powder is cooled to 25° C.

Example 10

Comparison

Adduct of 2-amino-1,3-propanediol (serinol), 2,5-hexanedione with carbon black.

The carbon black used is Carbon Black N326 (CB) (Cabot), with the following characteristics: 30 nm average diameter of the spherical particles, surface area equal to 77 m$^2$/g (determined by nitrogen absorption), absorption of DBP equal to 85 mL/100 g. The serinol used is Bracco and the 2,5-hexanedione was acquired from Aldrich.

A 100-mL single-neck flask is charged with 2.5 g of carbon black and 15 mL of acetone. The suspension is sonicated in an ultrasonic bath for 15 minutes. After this time, the following are added successively: 0.316 g of serinol and 0.396 g of 2,5-hexanedione. The resultant suspension is sonicated for 15 minutes. The solvent is removed at reduced pressure. A powder is obtained, consisting of serinol and 2,5-hexanedione, absorbed on the carbon black.

The powder is put in a 100-mL flask equipped with a magnetic stirrer and is heated at a temperature of 180° C. for 2 hours. After this time, the powder is cooled to 25° C.

A suspension in water was prepared with the sample of treated carbon black after heating at 180° C. for 2 hours. The suspension, having a concentration equal to 1 mg/mL, was sonicated for 10 minutes and was analysed by ultraviolet (UV) spectroscopy. UV spectra were recorded immediately after sonication and after 24 hours and they showed the same absorbance.

Example 11

Invention

Pyrrole, N-hexyl-2,5-dimethylpyrrole synthesized by mixing hexanamine with 2,5-hexanedione at 150° C. for 1 hour, silica and carbon black were used in this example.

Adduct of N-hexyl-2,5-dimethylpyrrole with carbon black and silica (carbon black/silica ratios 1/1 by weight).

The carbon black used is Carbon Black N326 (CB) (Cabot), with the following characteristics: 30 nm average diameter of the spherical particles, surface area equal to 77 m$^2$/g (determined by nitrogen absorption), absorption of DBP equal to 85 mL/100 g. The silica used is Zeosil 1165 MP (Rhodia). The serinol used is Bracco and the 2,5-hexanedione was acquired from Aldrich.

A 100-mL single-neck flask is charged with 1 g of carbon black and 15 mL of acetone. The suspension is sonicated in an ultrasonic bath for 15 minutes. After this time, the following are added successively: 0.248 g of N-hexyl-2,5-dimethylpyrrole and silica (1 g). The resultant suspension is sonicated for 15 minutes. The solvent is removed at reduced pressure. A powder is obtained, consisting of N-hexyl-2,5-dimethylpyrrole absorbed on the mixture of carbon black and silica.

The powder is put in a 100-mL flask equipped with a magnetic stirrer and is heated at a temperature of 180° C. for 2 hours. After this time, the powder is cooled to 25° C.

Example 12

Invention

In this example the pyrrole, N-hexyl-2,5-dimethylpyrrole, synthesized by mixing hexanamine with 2,5-hexanedione at 150° C. for 1 hour, silica and a high surface area graphite (HSAG) were used.

Adduct of N-hexyl-2,5-dimethylpyrrole with HSAG and silica (HSAG/silica ratios 1/1 by weight).

The graphite used is Synthetic Graphite 8427, acquired from Asbury Graphite Mills Inc., with a minimum carbon content of 99.8 wt. % and a surface area of 330 m$^2$/g. The silica used is Zeosil 1165 MP (Rhodia). The hexanamine and 2,5-hexanedione were acquired from Aldrich.

A 100-mL single-neck flask is charged with 1 g of HSAG and 15 mL of acetone. The suspension is sonicated in an ultrasonic bath for 15 minutes. After this time, the following are added successively: 0.248 g of N-hexyl-2,5-dimethylpyrrole and silica (1 g). The resultant suspension is sonicated for 15 minutes. The solvent is removed at reduced pressure. A powder is obtained, consisting of N-hexyl-2,5-dimethylpyrrole absorbed on the mixture of HSAG and silica.

The powder is put in a 100-mL flask equipped with a magnetic stirrer and is heated at a temperature of 180° C. for 2 hours. After this time, the powder is cooled to 25° C.

Example 13

Invention

A pyrrole acquired from Aldrich, 1,2,5-trimethylpyrrole, silica and carbon black were used in this example.

Adduct of 1,2,5-trimethylpyrrole with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia).

A 100-mL single-neck flask is charged with 1 g of carbon black and 15 mL of acetone. The suspension is sonicated in an ultrasonic bath for 15 minutes. After this time, the following are added successively: 0.188 g of 1,2,5-trimethylpyrrole and silica (1 g). The resultant suspension is sonicated for 15 minutes. The solvent is removed at reduced pressure. A powder is obtained, consisting of 1,2,5-trimethylpyrrole absorbed on the mixture of carbon black and silica.

The powder is put in a 100-mL flask equipped with a magnetic stirrer and is heated at a temperature of 180° C. for 2 hours. After this time, the powder is cooled to 25° C.

Example 14

Invention

A pyrrole acquired from Aldrich, 1,2,5-trimethylpyrrole, silica and a high surface area graphite (HSAG) were used in this example.

Adduct of 1,2,5-trimethylpyrrole with HSAG and silica (HSAG/silica ratios 1/1 by weight).

The graphite used is Synthetic Graphite 8427, acquired from Asbury Graphite Mills Inc., with a minimum carbon content of 99.8 wt. % and a surface area of 330 $m^2/g$. The silica used is Zeosil 1165 MP (Rhodia). The 1,2,5-trimethylpyrrole was acquired from Aldrich.

A 100-mL single-neck flask is charged with 1 g of HSAG and 15 mL of acetone. The suspension is sonicated in an ultrasonic bath for 15 minutes. After this time, the following are added successively: 0.188 g of 1,2,5-trimethylpyrrole and silica (1 g). The resultant suspension is sonicated for 15 minutes. The solvent is removed at reduced pressure. A powder is obtained, consisting of 1,2,5-trimethylpyrrole absorbed on the mixture of HSAG and silica.

The powder is put in a 100-mL flask equipped with a magnetic stirrer and is heated at a temperature of 180° C. for 2 hours. After this time, the powder is cooled to 25° C.

Example 15

Invention

Adduct of 2-amino-1,3-propanediol (serinol), 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The serinol used is Bracco and the 2,5-hexanedione was acquired from Aldrich.

A 100-mL single-neck flask equipped with a magnetic stirrer is charged with 0.316 g of serinol, 0.396 g of 2,5-hexanedione and 10 mL of acetone. A suspension of 2.5 g of carbon black and 2.5 g of silica in 15 mL of acetone is added to the mixture. The suspension is sonicated in an ultrasonic bath for 15 minutes. The solvent is removed at reduced pressure. A powder is obtained, consisting of serinol and 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

A suspension in water was prepared with the sample of treated carbon black after heating at 180° C. for 2 hours. The suspension, having a concentration equal to 1 mg/mL, was sonicated for 10 minutes and was analysed by ultraviolet (UV) spectroscopy. UV spectra were recorded immediately after sonication and after 24 hours and they showed the same absorbance.

Example 16

Invention

Adduct of hexanamine, 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). Hexanamine and 2,5-hexanedione were acquired from Aldrich. A 100-mL single-neck flask equipped with a magnetic stirrer is charged with 0.558 g of hexanamine, 0.630 g of 2,5-hexanedione and 10 mL of acetone. A suspension of 2.5 g of carbon black and 2.5 g of silica in 15 mL of acetone is added to the mixture. The suspension is sonicated in an ultrasonic bath for 15 minutes. The solvent is removed at reduced pressure. A powder is obtained, consisting of hexanamine and 2,5-hexanedione absorbed on the mixture of carbon black and silica.

The powder is put in a 100-mL flask equipped with a magnetic stirrer and is heated at a temperature of 180° C. for 2 hours. After this time, the powder is cooled to 25° C.

Example 17

Invention

Adduct of 2-amino-1,3-propanediol (serinol), 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The serinol used is Bracco and the 2,5-hexanedione was acquired from Aldrich.

A 100-mL single-neck flask equipped with a magnetic stirrer is charged with 0.316 g of serinol, 0.396 g of 2,5-hexanedione, 2.5 g of silica and 10 mL of acetone. The mixture is first stirred at room temperature, and then is dried at reduced pressure. 2.5 g of carbon black is added to the powder thus obtained and it is stirred at 180° C. for 2 hours. After this time, the powder is cooled to 25° C.

A suspension in water was prepared with the sample of treated carbon black after heating at 180° C. for 2 hours. The suspension, having a concentration equal to 1 mg/mL, was sonicated for 10 minutes and was analysed by ultraviolet (UV) spectroscopy. UV spectra were recorded immediately after sonication and after 24 hours and they showed the same absorbance.

Example 18

Invention

Adduct of hexanamine, 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The hexanamine and 2,5-hexanedione were acquired from Aldrich.

A 100-mL single-neck flask equipped with a magnetic stirrer is charged with 0.558 g of hexanamine, 0.630 g of 2,5-hexanedione, 2.5 g of silica and 10 mL of acetone. The mixture is first stirred at room temperature, and then is dried at reduced pressure. 2.5 g of carbon black is added to the powder thus obtained and it is stirred at 180° C. for 2 hours. After this time, the powder is cooled to 25° C.

Example 19

Invention

Adduct of 2-amino-1,3-propanediol (serinol), 2,5-hexanedione with carbon black and silica (carbon black/silica ratios 1/1 by weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The serinol used is Bracco and the 2,5-hexanedione was acquired from Aldrich.

A 100-mL single-neck flask equipped with a magnetic stirrer is charged with 0.316 g of serinol, 0.396 g of 2,5-hexanedione, 2.5 g of silica. The mixture is first stirred at room temperature and then is sonicated. 2.5 g of carbon black is added to the powder thus obtained and it is stirred at 180° C. for 2 hours. After this time, the powder is cooled to 25° C.

A suspension in water was prepared with the sample of treated carbon black after heating at 180° C. for 2 hours. The suspension, having a concentration equal to 1 mg/mL, was sonicated for 10 minutes and was analysed by ultraviolet (UV) spectroscopy. UV spectra were recorded immediately after sonication and after 24 hours and they showed the same absorbance.

Example 20

Invention

Adduct of Hexanamine, 2,5-Hexanedione with Carbon Black and Silica (Carbon Black/Silica Ratios 1/1 by Weight).

The carbon black used is Carbon Black N326 (CB) (Cabot), with the following characteristics: 30 nm average diameter of the spherical particles, surface area equal to 77 $m^2/g$ (determined by nitrogen absorption), absorption of DBP equal to 85 mL/100 g. The silica used is Zeosil 1165 MP (Rhodia). The hexanamine and 2,5-hexanedione were acquired from Aldrich.

A 100-mL single-neck flask equipped with a magnetic stirrer is charged with 0.558 g of hexanamine, 0.630 g of 2,5-hexanedione, 2.5 g of silica. The mixture is first stirred at room temperature and then sonicated. 2.5 g of carbon black is added to the powder thus obtained and it is stirred at 180° C. for 2 hours. After this time, the powder is cooled to 25° C.

Example 21

Adduct of 1,2,5-Trimethylpyrrole with HSAG (HSAG/TMP Ratios 6.6/1 by Weight)

A pyrrole acquired from Aldrich, 1,2,5-trimethylpyrrole and a high surface area graphite (HSAG) were used in this example.

The graphite used is Synthetic Graphite 8427, acquired from Asbury Graphite Mills Inc., with a minimum carbon content of 99.8 wt. % and a surface area of 330 $m^2/g$. The 1,2,5-trimethylpyrrole was acquired from Aldrich.

A 100-mL single-neck flask is charged with 1 g of HSAG (0.014 mol) and 15 mL of acetone. The suspension is sonicated in an ultrasonic bath for 15 minutes. After this time, 0.151 g (0.0014 mol) of 1,2,5-trimethylpyrrole is added. The resultant suspension is sonicated for 15 minutes. The solvent is removed at reduced pressure. A powder is obtained, consisting of 1,2,5-trimethylpyrrole absorbed on HSAG.

The powder is put in a 100-mL flask equipped with a magnetic stirrer and is stirred for 2 hours.

Example 22

Adduct of 1,2,5-trimethylpyrrole with HSAG (HSAG/TMP Ratios 6.6/1 by Weight)

A pyrrole acquired from Aldrich, 1,2,5-trimethylpyrrole and a high surface area graphite (HSAG) were used in this example.

The graphite used is Synthetic Graphite 8427, acquired from Asbury Graphite Mills Inc., with a minimum carbon content of 99.8 wt. % and a surface area of 330 $m^2/g$. The 1,2,5-trimethylpyrrole was acquired from Aldrich.

A 100-mL single-neck flask is charged with 1 g of HSAG (0.014 mol) and 15 mL of acetone. The suspension is sonicated in an ultrasonic bath for 15 minutes. After this time, 0.151 g (0.0014 mol) of 1,2,5-trimethylpyrrole is added. The resultant suspension is sonicated for 15 minutes. The solvent is removed at reduced pressure. A powder is obtained, consisting of 1,2,5-trimethylpyrrole absorbed on HSAG.

The powder is put in a 100-mL flask equipped with a magnetic stirrer and it is stirred at 180° C. for 2 hours. After this time, the powder is cooled to 25° C.

The adduct that formed was washed in a Soxhlet with acetone for 8 hours. After washing, the powder was recovered and was analysed by infrared spectroscopy.

Example 23

Adduct of 1,2,5-Trimethylpyrrole with HSAG (HSAG/TMP Ratios 0.66/1 by Weight)

A pyrrole acquired from Aldrich, 1,2,5-trimethylpyrrole and a high surface area graphite (HSAG) were used in this example.

The graphite used is Synthetic Graphite 8427, acquired from Asbury Graphite Mills Inc., with a minimum carbon content of 99.8 wt. % and a surface area of 330 m$^2$/g. The 1,2,5-trimethylpyrrole was acquired from Aldrich.

A 100-mL single-neck flask is charged with 1 g of HSAG (0.014 mol) and 15 mL of acetone. The suspension is sonicated in an ultrasonic bath for 15 minutes. After this time, 1.51 g (0.014 mol) of 1,2,5-trimethylpyrrole is added. The resultant suspension is sonicated for 15 minutes. The solvent is removed at reduced pressure. A powder is obtained, consisting of 1,2,5-trimethylpyrrole absorbed on HSAG.

The powder is put in a 100-mL flask equipped with a magnetic stirrer and it is stirred at 180° C. for 2 hours. After this time, the powder is cooled to 25° C.

The adduct that formed was washed in a Soxhlet with acetone for 8 hours. After washing, the washing acetone was dried at reduced pressure. An amber-coloured oil was isolated, and was analysed by $^1$H NMR spectroscopy.

Example 24

Adduct of 1,2,5-Trimethylpyrrole with HSAG (HSAG/TMP Ratios 0.0066/1 by Weight)

A pyrrole acquired from Aldrich, 1,2,5-trimethylpyrrole and a high surface area graphite (HSAG) were used in this example.

The graphite used is Synthetic Graphite 8427, acquired from Asbury Graphite Mills Inc., with a minimum carbon content of 99.8 wt. % and a surface area of 330 m$^2$/g. The 1,2,5-trimethylpyrrole was acquired from Aldrich.

A 50-mL single-neck flask is charged with 0.01 g of HSAG (1.3810$^{-4}$ mol) and 5 mL of acetone. The suspension is sonicated in an ultrasonic bath for 15 minutes. After this time, 1.51 g (0.014 mol) of 1,2,5-trimethylpyrrole is added. The resultant suspension is sonicated for 15 minutes. The solvent is removed at reduced pressure. The flask containing the reaction mixture is equipped with a magnetic stirrer. It is stirred at 180° C. for 2 hours. After this time, the reaction mixture is first left to cool to 25° C. and then is dissolved in dichloromethane and then is filtered on a Büchner. The washing dichloromethane is dried at reduced pressure. An amber-coloured oil was isolated, and was analysed by $^1$H NMR spectroscopy.

Example 25

Invention: Adduct of Serinol Pyrrole with HSAG (HSAG/SP Ratio 10/1 by Weight)

In this example the serinol pyrrole used was synthetized by mixing serinol with 2,5-hexanedione, in equimolar ratio, at 150° C. for 3 hours. The serinol used is from Bracco and 2,5-hexanedione was acquired from Aldrich.

The graphite used is Synthetic Graphite 8427, acquired from Asbury Graphite Mills Inc., with a minimum carbon content of 99.8 wt. % and a surface area of 330 m$^2$/g.

A 100-mL single-neck flask is charged with 1 g of HSAG and 15 mL of acetone. The suspension is sonicated in an ultrasonic bath for 15 minutes. After this time, 0.100 g of serinol pyrrole are added. The resultant suspension is sonicated for 15 minutes. The solvent is removed at reduced pressure. A powder, consisting of serinol pyrrole on HSAG (HSAG/SP), is obtained. Said powder is heated at 150° C. for 2 hours.

Example 26

Invention: Adduct of Serinol Pyrrole with CBN234 (CBN234/SP Ratio 10/1 by Weight)

In this example the serinol pyrrole used was synthetized by mixing serinol with 2,5-hexanedione, in equimolar ratio, at 150° C. for 3 hours.

The Carbon black (CB) used is Vulcan 7H from Cabot, corresponding to a Carbon Black N234, with a surface area of 113 m$^2$/g.

A 100-mL single-neck flask is charged with 1 g of CBN234 and 15 mL of acetone. The suspension is sonicated in an ultrasonic bath for 15 minutes. After this time, 0.100 g of serinol pyrrole are added. The resultant suspension is sonicated for 15 minutes. The solvent is removed at reduced pressure. A powder, consisting of serinol pyrrole on CBN234 (CBN234/SP), is obtained. Said powder is heated at 150° C. for 2 hours.

Example 27

Invention: Adduct of Sepiolite and HSAG/SP

In a 100 mL beaker were subsequently introduced: HSAG/SP (1 g), obtained according to example 25, and H$_2$O (100 mL). The suspension was sonicated for 15 minutes with a probe-type sonicator. After this time, the HSAG/SP suspension in water was poured into a 250 mL beaker, which had been previously charged with 1 g of sepiolite and 100 mL of water. The thus obtained suspension, containing HSAG/SP and sepiolite in water, was left stirring for 30 minutes at room temperature and then at 50° C. for 30 minutes. After this time, the mixture is centrifuged at 9000 rpm for 30 minutes. The solid precipitate is removed and dried in an oven.

Example 28

Invention: Adduct of Sepiolite and the Adduct of HSAG with Hexyl Pyrrole (HSAG/EP)

In this example the hexyl pyrrole used was synthetized by mixing hexanamine with 2,5-hexanedione, in equimolar ratio, at 130° C. for 3 hours. The hexanamine and 2,5-hexanedione used were acquired from Aldrich.

The adduct of HSAG and hexyl pyrrole (HSAG/EP) was obtained with the same procedure described in example 25 for the adduct HSAG/SP, using hexyl pyrrole instead of serinol pyrrole.

The adduct of sepiolite and HSAG/EP was obtained with the same procedure described in example 27 for the adduct of sepiolite and HSAG/SP, using HSAG/EP instead of HSAG/SP.

Example 29

Invention: Adduct of Sepiolite and the Adduct of HSAG with Dodecyl Pyrrole (HSAG/DDcP)

In this example the dodecyl pyrrole used was synthetized by mixing dodecylamine with 2,5-hexanedione, in equimolar ratio, at 130° C. for 3 hours. The dodecylamine and 2,5-hexanedione used were acquired from Aldrich.

The adduct of HSAG and dodecyl pyrrole (HSAG/DDcP) was obtained with the same procedure described in example 25 for the adduct HSAG/SP, using dodecyl pyrrole instead of serinol pyrrole.

The adduct of sepiolite and HSAG/DDcP was obtained with the same procedure described in example 27 for the adduct of sepiolite and HSAG/SP, using HSAG/DDcP instead of HSAG/SP.

Example 30

Invention: Adduct of Sepiolite and CBN234/SP

The adduct of sepiolite and CBN234/SP was obtained with the same procedure described in example 27 for the adduct of sepiolite and HSAG/SP, using CBN234/SP, obtained according to example 26, instead of HSAG/SP.

Example 31

Invention: Adduct of Sepiolite and HSAG/SP from Aqueous Dispersion

In a 100 mL beaker were subsequently introduced: HSAG/SP (1 g), obtained according to example 25, and $H_2O$ (100 mL). The suspension was sonicated for 15 minutes with a probe-type sonicator. After this time, the HSAG/SP suspension in water was poured into a 250 mL beaker, which had been previously charged with 2 g of sepiolite and 100 mL of water. The thus obtained suspension, containing HSAG/SP and sepiolite in water, was left stirring for 12 hours at room temperature. After this time, the adduct of sepiolite and HSAG/SP is precipitated and it is removed by filtration on buchner.

Tests of Extraction of Organic Substances from the Adducts in Table 1

Tables 2A and 2B give the results of the tests of extraction of organic substances from the adducts, whose preparation has been described in examples 1-20.

TABLE 2A

Tests of extraction of the pyrrole compound from the adducts in Table 1.[a]

| | Adduct from Example No. | | | | | | |
|---|---|---|---|---|---|---|---|
| | 1 | 2 | 3 | 4 | 5 | 6 | 7 |
| Pyrrole compound in washing $H_2O$ | No | No | No | No | No | No | Yes |

[a]The table gives the reply to the question: was an organic substance observed, by GC-MS analysis, in the extraction solution?

TABLE 2B

Tests of extraction of the pyrrole compound from the adducts in Table 1.[a]

| | Adduct from Example No. | | | | | | | | | | | |
|---|---|---|---|---|---|---|---|---|---|---|---|---|
| | 8 | 9 | 10 | 11 | 13 | 14 | 15 | 16 | 17 | 18 | 19 | 20 |
| Pyrrole compound in washing $H_2O$ | /[b] | /[c] | Yes | No | No | No | No | No | No | No | No | No |

[a]The table gives the reply to the question: was an organic substance observed, by GC-MS analysis, in the extraction solution?;
[b]was the presence of 2,5-hexanedione detected in the wash water?;
[c]was the presence of serinol detected in the wash water?

The extraction test and analysis of the solution obtained from extraction were carried out as given in the description of the experimental procedures, preparation of the adducts and characterization.

To summarize, Table 2 gives the reply to the question: was at least one organic substance observed, by GC-MS analysis, in the extraction solution of the adduct?

The adducts prepared in examples 1, 2 and 3 do not release any organic substance during the extraction test. In fact, "No" is reported in the first 3 columns of Table 2. "Yes" is reported in the columns of Table 2 relating to the tests for extraction of the adducts prepared in examples 7, 8, 9 and 10. This signifies that the adducts prepared in examples 7, 8, 9 and 10 release at least one organic substance.

The adducts prepared in examples 4, 5, 6, 15, 16, 17, 18, 19, 20 were prepared with a carbon allotrope/silica ratio equal to 1:1. The tests for extraction of the adducts prepared in these tests did not lead to extraction of any organic substance.

This result was obtained by preparing the adducts with various amines (serinol, hexanamine, (3-aminopropyl) triethoxysilane), various carbon allotropes (carbon black, high surface area graphite with nanometric dimensions), various inorganic oxides-hydroxides (silica, montmorillonite), and various methods of preparation (mixing the components of the adduct in a liquid or in the solid state). These results thus suggest that a sufficient amount of silica makes it possible to prevent extraction of organic substances from the adducts, provided they are formed from all the components envisaged by the present invention, even varying other conditions such as the type of amine, type of carbon allotrope, and type of inorganic oxide-hydroxide.

Organic substances were detected in the extracts of the adducts prepared in examples 7, 8, 9 and 10, even though adducts 8 and 9 were prepared with a carbon black/silica ratio equal to 1:1. These results demonstrate that all components of the adducts must be present to avoid extractability of organic substances from said adducts.

Tests of Stability of Dispersions in $H_2O$ of the Adducts in Table 1

Tables 3A and 3B give the results of the tests of absorbance in the UV-Visible region, of the aqueous solutions of the adducts prepared in examples 1-20.

TABLE 3A

Tests of stability of dispersions in $H_2O$ of the adducts in Table 1. Absorbance measured at 300 nm

| | Adduct from Example No. | | | | | | |
|---|---|---|---|---|---|---|---|
| | 1 | 2 | 3 | 4 | 5 | 6 | 7 |
| Absorbance at t = 0 ($A_{t=0}$) | 4.11 | 4.11 | 4.11 | 4.11 | 2.93 | 4.11 | 0 |
| Delta absorbance ($A_{t=0} - (A_{t=168h})$) | 0 | 0 | 0 | 0 | 0.36 | 0 | = |

TABLE 3B

Tests of stability of dispersions in H₂O of the adducts in
Table 1. Absorbance measured at 300 nm

| | Adduct from Example No. | | | | | | | | | | | | |
|---|---|---|---|---|---|---|---|---|---|---|---|---|---|
| | 8 | 9 | 10 | 11 | 12 | 13 | 14 | 15 | 16 | 17 | 18 | 19 | 20 |
| Absorbance at t = 0 ($A_{t=0}$) | 0 | 0 | 0 | 0.89 | 1 | 4.05 | 4.0 | 4.11 | 2.89 | 4.11 | 2.91 | 4.11 | 2.90 |
| Delta absorbance ($A_{t=0} - A_{t=168h}$) | = | = | = | 0.57 | 0.50 | 0 | 0 | 0 | 0.40 | 0 | 0.38 | 0 | 0.41 |

Preparation of the solutions and analysis of absorption were carried out as given in the description of the experimental procedures. In particular, Table 3 gives the values of absorbance measured at the end of preparation of the dispersions (time=0) and after 7 days (time=168 hours) in which the dispersions were held without stirring.

The dispersions in water prepared with the adducts obtained from examples 1-4 showed the same high absorbance at time=0 and after 7 days. These results show that the adduct that contains serinol has a hydrophilic character, over a wide range of (carbon black)/(inorganic oxide-hydroxide) weight ratios, with silica or montmorillonite as the oxide-hydroxide. Entirely similar results were obtained with the adducts prepared in examples 15, 17 and 19, in which the amine is always serinol and various methods were employed for preparing the adducts, methods that are different from one another and are different from the method in example 1. Thus, changing the method for preparing the adduct does not alter the dispersibility in water of the adduct formed starting from serinol. Similar results were obtained with the adduct prepared in example 6, which has (3-aminopropyl)triethoxysilane as the amine.

The dispersions in water prepared with the adducts obtained from example 5 showed a lower absorbance relative to that obtained with the adducts from examples 1-4 and showed an appreciable reduction in absorbance after seven days. This result may be attributed to the use of an amine with lipophilic character. The smaller absorbance and greater relative reduction of absorbance obtained with the adduct in example 5 may be attributed to the use of a larger amount of silica. Results entirely similar to those obtained with the adduct of example 5 were obtained with the adducts of examples 16, 18 and 20. As already commented for the absorbance of the adducts formed starting from serinol, changing the method of preparation of the adduct does not alter its dispersibility in water.

The tests of absorbance of the adducts formed starting from the pyrrole compounds already formed gave results entirely similar to those obtained with the adducts formed starting from diketone and amine, for the same substituent of the nitrogen atom. This is found on comparing the absorbances obtained with the adduct from example 11 and with the adducts from examples 5, 16, 18 and 20. In these examples, a hexyl radical is the substituent of the nitrogen. The absorbance obtained with the adduct from example 12 is similar.

The adducts formed in examples 7, 8, 9 and 10 do not cause any absorbance when dispersed in water. This indicates that these adducts do not remain in suspension. Each of these adducts lacks one component relative to the adduct according to the present invention.

It should be noted that the adducts from examples 13 and 14 show absorbance, similar to that obtained with the adducts formed starting from serinol. This is certainly a noteworthy and interesting result, since trimethylpyrrole is a molecule that is certainly lipophilic, which should not impart a hydrophilic character to the adduct. This result may lead to the presumption of a mechanism for formation of the adduct that involves the formation of polar groups also starting from trimethylpyrrole.

Tests of Stability of Dispersions in Toluene of the Adducts in Table 1

Table 4 gives the results of the tests of absorbance in the UV-Visible region of the toluene solutions of the adducts prepared in examples 5, 11 and 16, i.e. of the adducts that contain the hexyl radical and that showed lower absorbance in water.

TABLE 4

Tests of stability of dispersions in toluene of the
adducts in Table 1. Absorbance measured at 300 nm

| Adduct from Example No. | 5 | 11 | 16 |
|---|---|---|---|
| Absorbance at t = 0 ($A_{t=0}$) | 4.11 | 4.11 | 4.11 |
| Delta absorbance ($A_{t=0} - A_{t=168\ h}$) | 0 | 0 | 0 |

It can be seen that the absorbance in toluene and the stability over time are greater than those in water and is similar for the three adducts, in line with the lipophilic character of the substituent of the nitrogen and thus of the amine and of the pyrrole compound.

The invention claimed is:

1. An adduct obtainable from:
a) a reaction product of a compound of formula (I)

wherein X is selected from the group consisting of

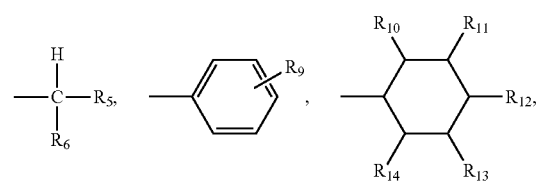

-continued

[chemical structure: trimethoxysilyl propyl group] and [chemical structure: glycerol-like CH2OH-CH-CH2OH];

wherein:

R$_5$ and R$_6$ are independently selected from the group consisting of hydrogen, C$_1$-C$_{18}$ alkyl, C$_2$-C$_{18}$ linear or branched alkenyl or alkynyl, aryl, C$_1$-C$_{22}$ linear or branched alkyl-aryl, C$_2$-C$_{22}$ linear or branched alkenyl-aryl, C$_2$-C$_{22}$ linear or branched alkynyl-aryl, and heteroaryl;

or at least one of R$_5$ or R$_6$ is independently

[chemical structure with subscripts m and n]

wherein m is chosen from 0, 1, and 2, and n is chosen from integers ranging from 1 to 30, and wherein if only one of R$_5$ and R$_6$ is

[chemical structure with subscripts m and n]

wherein m is chosen from 0, 1, and 2, and n is chosen from integers ranging from 1 to 30, then the other is selected from the group consisting of hydrogen, C$_1$-C$_{18}$ alkyl, and C$_2$-C$_{18}$ linear or branched alkenyl or alkynyl;

or at least one of R$_5$ and R$_6$ is:

[chemical structure with Si(R$_7$)(R$_7'$)(R$_7''$) and subscript n]

wherein n is chosen from 0, 1, 2, and 3, and R$_7$, R$_7'$, and R$_7''$ are independently selected from the group consisting of C$_1$-C$_4$ alkyl and C$_1$-C$_4$ oxygen-alkyl;

or at least one of R$_5$ and R$_6$ is

[chemical structure with N(R$_8$)(R$_8'$) and subscript n]

wherein n is chosen from integers ranging from 0 to 10;

and R$_8$ and R$_8'$ are independently selected from the group consisting of hydrogen and C$_1$-C$_4$ alkyl;

or at least one of R$_5$ and R$_6$ is

[pyrrole structure with subscript n]

wherein n is chosen from integers ranging from 1 to 10;

or at least one of R$_5$ and R$_6$ is

[chemical structure: –OR$_{15}$]

and R$_{15}$ is selected from the group consisting of hydrogen, C$_1$-C$_{22}$ linear or branched alkyl, C$_2$-C$_{22}$ linear or branched alkenyl or alkynyl, aryl, C$_1$-C$_{22}$ linear or branched alkyl-aryl, C$_2$-C$_{22}$ linear or branched alkenyl-aryl, C$_2$-C$_{22}$ linear or branched alkynyl-aryl, linear or branched C$_2$-C$_{22}$ acyl-alkyl, linear or branched C$_3$-C$_{22}$ acyl-alkenyl or acyl-alkynyl, acyl-aryl, acyl-alkyl-aryl with linear or branched C$_2$-C$_{22}$ acyl-alkyl, acyl-alkenyl-aryl with linear or branched C$_3$-C$_{22}$ acyl-alkenyl, acyl-alkynyl-aryl with linear or branched C$_3$-C$_{22}$ acyl-alkynyl, and heteroaryl;

or at least one of R$_5$ and R$_6$ is

[chemical structure: C(=O)OR$_{19}$]

and R$_{19}$ is selected from the group consisting of hydrogen, C$_1$-C$_{22}$ linear or branched alkyl, C$_2$-C$_{22}$ linear or branched alkenyl or alkynyl, aryl, C$_1$-C$_{22}$ linear or branched alkyl-aryl, C$_2$-C$_{22}$ linear or branched alkenyl-aryl, C$_2$-C$_{22}$ linear or branched alkynyl-aryl, and heteroaryl;

R$_9$ is selected from the group consisting of hydrogen, alkyl, aryl, benzyl, amine, alkylamine, arylamine, benzylamine, and aminoaryl;

R$_{10}$, R$_{11}$, R$_{12}$, R$_{13}$ and R$_{14}$ are independently selected from the group consisting of hydrogen, C$_1$-C$_{18}$ alkyl, C$_2$-C$_{18}$ linear or branched alkenyl or alkynyl, and 1-(4-aminocyclohexyl)methylene;

with a compound of formula (II)

[chemical structure of formula (II) with R$_{18}$, R$_{17}$, R$_{16}$ and subscripts z, y, n, m] (II)

wherein n is chosen from integers ranging from 1 to 1000, m is chosen from integers ranging from 1 to 1000, y is chosen from 0 and 1, and z is chosen from 0 and 1;

and wherein R$_{16}$ is selected from the group consisting of hydrogen and methyl;

and $R_{17}$ and $R_{18}$ are selected from the group consisting of hydrogen, $C_2$-$C_{30}$ linear or branched alkyl, alkenyl or alkynyl, aryl, $C_2$-$C_{30}$ alkyl-aryl, $C_2$-$C_{30}$ linear or branched alkenyl-aryl, $C_2$-$C_{30}$ alkynyl-aryl, and heteroaryl;

b) a carbon allotrope with $sp^2$ hybridized carbon atoms; and c) an inorganic oxide-hydroxide.

2. The adduct according to claim 1, wherein the carbon allotrope with $sp^2$ hybridized carbon atoms is selected from the group consisting of graphene, nano-graphites consisting of few graphene layers, graphite, fullerene, nanotoroids, nanocones, graphene nanoribbons, single-wall or multi-wall carbon nanotubes, and carbon black.

3. The adduct according to claim 1, wherein the carbon allotrope comprises functional groups selected from the group consisting of:
oxygenated functional groups;
functional groups containing carbonyls;
functional groups containing nitrogen atoms; and
functional groups containing sulfur atoms.

4. The adduct according to claim 3, wherein the oxygenated functional groups of the carbon allotrope are chosen from hydroxyls and epoxides.

5. The adduct according to claim 3, wherein the functional groups containing carbonyls of the carbon allotrope are chosen from aldehydes, ketones, and carboxylic acids.

6. The adduct according to claim 3, wherein the functional groups containing nitrogen atoms of the carbon allotrope are chosen from amines, amides, nitriles, diazonium salts, and imines.

7. The adduct according to claim 3, wherein the functional groups containing sulfur atoms of the carbon allotrope are chosen from sulphides, disulfides, mercaptans, sulfones, and sulfinic and sulfonic groups.

8. The adduct according to claim 1, wherein the oxide-hydroxide is selected from the group consisting of silica, layer silicates, fibrillar silicates, mixed oxides of aluminium and magnesium with lamellar structure, and alumina.

9. The adduct according to claim 8, wherein the layer silicates have a thickness of a single layer ranging from 0.1 to 30 nm.

10. The adduct according to claim 9, wherein the thickness ranges from 0.5 to 15 nm, or from 0.8 to 2 nm.

11. The adduct according to claim 9, wherein the layer silicates are selected from the group consisting of serpentine, kaolin, talc, pyrophyllite, smectites, vermiculite, mica, chlorite, palygorskite, sepiolite, allophane, imogolite, and hydrotalcite.

12. The adduct according to claim 11, wherein the layer silicates are smectites chosen from montmorillonite, bentonite, beidellite, nontronite, volkonskoite, hectorite, fluorohectorite, laponite, saponite, stevensite, and sauconite.

13. The adduct according to claim 11, wherein the layer silicates are micas chosen from celadonite, lepidolite, muscovite, and phlogopite.

14. A process for preparing an adduct comprising:
reacting a compound of formula (I) with a compound of formula (II) to obtain a compound of formula (III) wherein formula (I) is

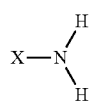
(I)

wherein
X is selected from the group consisting of

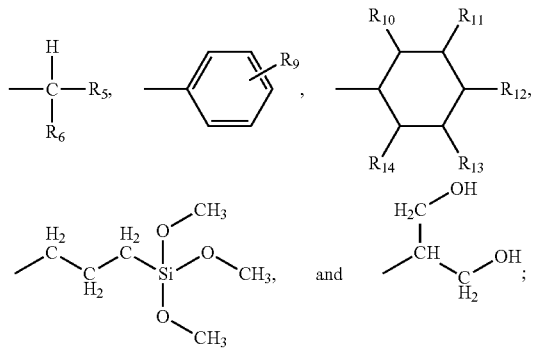

wherein:
$R_5$ and $R_6$ are independently selected from the group consisting of hydrogen, $C_1$-$C_{18}$ alkyl, $C_2$-$C_{18}$ linear or branched alkenyl or alkynyl, aryl, $C_1$-$C_{22}$ linear or branched alkyl-aryl, $C_2$-$C_{22}$ linear or branched alkenyl-aryl, $C_2$-$C_{22}$ linear or branched alkynyl-aryl, and heteroaryl;
or at least one of $R_5$ or $R_6$ is independently

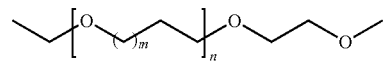

wherein m is chosen from 0, 1, and 2, and n is chosen from integers ranging from 1 to 30,
and wherein if only one of $R_5$ and $R_6$ is

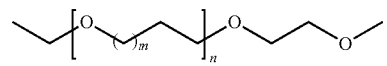

wherein m is chosen from 0, 1, and 2, and n is chosen from integers ranging from 1 to 30,
then the other is selected from the group consisting of hydrogen, $C_1$-$C_{18}$ alkyl, and $C_2$-$C_{18}$ linear or branched alkenyl or alkynyl;
or at least one of $R_5$ and $R_6$ is:

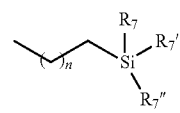

wherein n is chosen from 0, 1, 2, and 3,
and $R_7$, $R_7'$, and $R_7''$ are independently selected from the group consisting of $C_1$-$C_4$ alkyl and $C_1$-$C_4$ oxygen-alkyl;
or at least one of $R_5$ and $R_6$ is

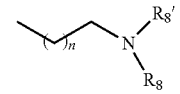

wherein n is chosen from integers ranging from 0 to 10;

and $R_8$ and $R_8'$ are independently selected from the group consisting of hydrogen and $C_1$-$C_4$ alkyl;

or at least one of $R_5$ and $R_6$ is

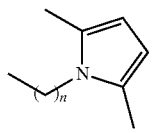

wherein n is chosen from integers ranging from 1 to 10;

or at least one of $R_5$ and $R_6$ is

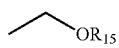

and $R_{15}$ is selected from the group consisting of hydrogen, $C_1$-$C_{22}$ linear or branched alkyl, $C_2$-$C_{22}$ linear or branched alkenyl or alkynyl, aryl, $C_1$-$C_{22}$ linear or branched alkyl-aryl, $C_2$-$C_{22}$ linear or branched alkenyl-aryl, $C_2$-$C_{22}$ linear or branched alkynyl-aryl, linear or branched $C_2$-$C_{22}$ acyl-alkyl, linear or branched $C_3$-$C_{22}$ acyl-alkenyl or acyl-alkynyl, acyl-aryl, acyl-alkyl-aryl with linear or branched $C_2$-$C_{22}$ acyl-alkyl, acyl-alkenyl-aryl with linear or branched $C_3$-$C_{22}$ acyl-alkenyl, acyl-alkynyl-aryl with linear or branched $C_3$-$C_{22}$ acyl-alkynyl, and heteroaryl;

or at least one of $R_5$ and $R_6$ is

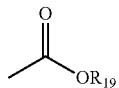

and $R_{19}$ is selected from the group consisting of hydrogen, $C_1$-$C_{22}$ linear or branched alkyl, $C_2$-$C_{22}$ linear or branched alkenyl or alkynyl, aryl, $C_1$-$C_{22}$ linear or branched alkyl-aryl, $C_2$-$C_{22}$ linear or branched alkenyl-aryl, $C_2$-$C_{22}$ linear or branched alkynyl-aryl, and heteroaryl;

$R_9$ is selected from the group consisting of hydrogen, alkyl, aryl, benzyl, amine, alkylamine, arylamine, benzylamine, and aminoaryl;

$R_{10}$, $R_{11}$, $R_{12}$, $R_{13}$ and $R_{14}$ are independently selected from the group consisting of hydrogen, $C_1$-$C_{18}$ alkyl, $C_2$-$C_{18}$ linear or branched alkenyl or alkynyl, and 1-(4-aminocyclohexyl)methylene;

wherein formula (II) is

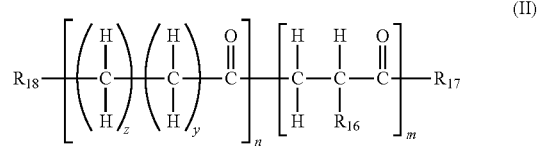

wherein n is chosen from integers ranging from 1 to 1000, m is chosen from integers ranging from 1 to 1000, y is chosen from 0 and 1, and z is chosen from 0 and 1;

and wherein $R_{16}$ is selected from the group consisting of hydrogen and methyl;

and $R_{17}$ and $R_{18}$ are selected from the group consisting of hydrogen, $C_2$-$C_{30}$ linear or branched alkyl, alkenyl or alkynyl, aryl, $C_2$-$C_{30}$ alkyl-aryl, $C_2$-$C_{30}$ linear or branched alkenyl-aryl, $C_2$-$C_{30}$ alkynyl-aryl, and heteroaryl; and and wherein formula (III) is

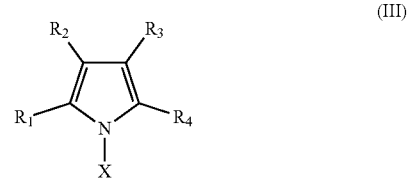

wherein $R_1$, $R_2$, $R_3$ and $R_4$ are independently selected from the group consisting of hydrogen, $C_1$-$C_3$ alkyl, $C_2$-$C_{18}$ linear or branched alkenyl or alkynyl, aryl, $C_1$-$C_{18}$ linear or branched alkyl-aryl, $C_2$-$C_{18}$ linear or branched alkenyl-aryl, $C_2$-$C_{22}$ linear or branched alkynyl-aryl, and heteroaryl;

reacting the compound of formula (III) with a carbon allotrope with sp² hybridized carbon atoms and an inorganic oxide-hydroxide by providing energy in a form chosen from thermal, mechanical, photon irradiation, and mixtures thereof to a mixture of the reactants in the presence of oxygen.

15. The process according to claim 14, wherein the thermal energy is provided at a temperature ranging from 50° C. to 180° C. and for a time ranging from 15 to 360 minutes.

16. The process according to claim 14, wherein the mechanical energy is provided for a time ranging from 15 to 360 minutes.

17. The process according to claim 14, wherein the photon irradiation energy is provided at a wavelength ranging from 200 to 380 nm and for a time ranging from 30 to 180 minutes.

* * * * *